US011737981B2

(12) United States Patent
Prud'Homme et al.

(10) Patent No.: US 11,737,981 B2
(45) Date of Patent: Aug. 29, 2023

(54) CELLULOSIC POLYMER NANOPARTICLES AND METHODS OF FORMING THEM

(71) Applicant: The Trustees of Princeton University, Princeton, NJ (US)

(72) Inventors: Robert K. Prud'Homme, Princeton, NJ (US); Jie Feng, Princeton, NJ (US); Kurt D. Ristroph, Princeton, NJ (US); Hoang (Jack) Lu, Princeton, NJ (US); Yingyue Zhang, Princeton, NJ (US); Simon A. McManus, Princeton, NJ (US); Robert F. Pagels, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 16 days.

(21) Appl. No.: 16/816,241

(22) Filed: Mar. 11, 2020

(65) Prior Publication Data

US 2020/0206136 A1    Jul. 2, 2020

Related U.S. Application Data

(63) Continuation of application No. PCT/US2018/050714, filed on Sep. 12, 2018.

(60) Provisional application No. 62/557,744, filed on Sep. 12, 2017.

(51) Int. Cl.
| | |
|---|---|
| *A61K 9/16* | (2006.01) |
| *B01J 13/08* | (2006.01) |
| *A61K 31/498* | (2006.01) |
| *A61K 31/135* | (2006.01) |
| *A61K 31/5377* | (2006.01) |
| *A61K 38/13* | (2006.01) |
| *A61K 31/496* | (2006.01) |
| *A61K 38/14* | (2006.01) |

(52) U.S. Cl.
CPC ............ *A61K 9/167* (2013.01); *A61K 9/1652* (2013.01); *A61K 31/135* (2013.01); *A61K 31/496* (2013.01); *A61K 31/498* (2013.01); *A61K 31/5377* (2013.01); *A61K 38/13* (2013.01); *A61K 38/14* (2013.01); *B01J 13/08* (2013.01)

(58) Field of Classification Search
None
See application file for complete search history.

(56) References Cited

U.S. PATENT DOCUMENTS

| | | |
|---|---|---|
| 4,342,653 A | 8/1982 | Halverson |
| 4,382,982 A | 5/1983 | Whillans |
| 4,888,238 A | 12/1989 | Katz et al. |
| 4,999,417 A | 3/1991 | Domb |
| 5,366,734 A | 11/1994 | Hutchinson |
| 5,578,325 A | 11/1996 | Domb et al. |
| 6,291,013 B1 * | 9/2001 | Gibson ................. B01J 13/125 264/4.1 |
| 6,383,500 B1 | 5/2002 | Wooley et al. |
| 6,610,653 B1 | 8/2003 | Backstrom et al. |
| 6,730,322 B1 | 5/2004 | Bernstein et al. |
| 7,977,024 B2 | 7/2011 | Zhou et al. |
| 8,137,699 B2 | 3/2012 | Johnson et al. |
| 8,288,001 B1 | 10/2012 | Fan et al. |
| 8,623,329 B1 | 1/2014 | Hansen et al. |
| 8,703,196 B2 | 4/2014 | Babcock et al. |
| 9,603,830 B2 | 3/2017 | Powell |
| 9,782,358 B2 | 10/2017 | Kataoka et al. |
| 10,231,937 B2 | 3/2019 | Pagels et al. |
| 11,103,461 B2 | 8/2021 | Prud'Homme et al. |
| 2004/0052824 A1 | 3/2004 | Abou Chacra-Vernet et al. |
| 2004/0091546 A1 | 5/2004 | Johnson et al. |
| 2004/0236050 A1 | 11/2004 | Lundquist et al. |
| 2005/0158390 A1 | 7/2005 | Rana et al. |
| 2005/0228074 A1 | 10/2005 | Warren et al. |
| 2006/0040831 A1 | 2/2006 | Cassidy et al. |
| 2006/0057215 A1 | 3/2006 | Raiche et al. |
| 2006/0078624 A1 | 4/2006 | Zalipsky et al. |
| 2006/0159921 A1 | 7/2006 | Murthy et al. |
| 2006/0224095 A1 | 10/2006 | Claverie et al. |
| 2006/0247383 A1 | 11/2006 | Hedrick et al. |
| 2007/0042498 A1 | 2/2007 | Ebner |
| 2007/0231355 A1 | 10/2007 | Quadir et al. |
| 2008/0145432 A1 | 6/2008 | Kakizawa et al. |
| 2008/0160305 A1 | 7/2008 | Warren et al. |
| 2009/0061009 A1 | 3/2009 | Schwarz et al. |
| 2009/0155326 A1 | 6/2009 | Mack et al. |
| 2009/0325292 A1 | 12/2009 | Baker et al. |
| 2010/0150994 A1 | 6/2010 | Kotyla |
| 2010/0203149 A1 | 8/2010 | Radosz et al. |
| 2010/0233251 A1 | 9/2010 | Von Andrian et al. |

(Continued)

FOREIGN PATENT DOCUMENTS

| | | | |
|---|---|---|---|
| CN | 100389766 C | * | 5/2008 |
| CN | 100389766 C | | 5/2008 |

(Continued)

OTHER PUBLICATIONS

Babu et al., "Solubility Advantage of Amorphous Drugs and Pharmaceutical Cocrystals", Crystal Growth & Design, vol. 11, pp. 2662-2679 (2011). (Year: 2011).*

Bailly et al., "Poly(N-vinylpyrrolidone)-block-poly(vinyl acetate) as a Drug Delivery Vehicle for Hydrophobic Drugs", vol. 13, pp. 4109-4117 (Nov. 2, 2012). (Year: 2012).*

Elchenausia et al., "RAFT/MAD IX emulsion copolymerization of vinyl acetate and N-vinylcaprolactam: towards waterbome physically crosslinked thermoresponsive particles", Polymer Chemistry, pp. 1-28 (2017). (Year: 2017).*

(Continued)

*Primary Examiner* — Dominic Lazaro
(74) *Attorney, Agent, or Firm* — Nixon & Vanderhye, P.C.; Lars H. Genieser

(57) ABSTRACT

Nanoparticles including a cellulosic polymer and a hydrophobic material and methods for forming them.

26 Claims, 20 Drawing Sheets

(56) References Cited

U.S. PATENT DOCUMENTS

| | | |
|---|---|---|
| 2010/0305219 A1 | 12/2010 | Granick et al. |
| 2010/0310649 A1 | 12/2010 | Richard et al. |
| 2010/0330368 A1 | 12/2010 | Prud'homme et al. |
| 2011/0012057 A1 | 1/2011 | Lindner et al. |
| 2011/0022129 A1 | 1/2011 | Prud'homme et al. |
| 2011/0064821 A1 | 3/2011 | Catchpole et al. |
| 2011/0200828 A1 | 8/2011 | Li et al. |
| 2011/0236686 A1 | 9/2011 | Kitano et al. |
| 2011/0293701 A1 | 12/2011 | Bratzler et al. |
| 2012/0009267 A1 | 1/2012 | Cho et al. |
| 2012/0041150 A1 | 2/2012 | Yabu et al. |
| 2012/0121510 A1 | 5/2012 | Brem et al. |
| 2012/0171254 A1 | 7/2012 | Johnson et al. |
| 2012/0230913 A1 | 9/2012 | Johnston et al. |
| 2012/0308640 A1 | 12/2012 | Percec et al. |
| 2013/0101516 A1 | 4/2013 | Zhao |
| 2013/0122058 A1 | 5/2013 | Chow et al. |
| 2013/0171208 A1 | 7/2013 | Smith et al. |
| 2013/0337078 A1 | 12/2013 | Mayer et al. |
| 2014/0037573 A1 | 2/2014 | Eliasof et al. |
| 2014/0099379 A1 | 4/2014 | Beck-Broichsitter et al. |
| 2014/0249235 A1 | 9/2014 | Brugel et al. |
| 2014/0302154 A1 | 10/2014 | Waldoefner et al. |
| 2014/0356443 A1 | 12/2014 | Brisander et al. |
| 2015/0086618 A1 | 3/2015 | Onyuksel et al. |
| 2015/0218198 A1* | 8/2015 | Petermann ........... A61K 9/4891 424/463 |
| 2015/0283218 A1 | 10/2015 | Shea et al. |
| 2015/0290233 A1 | 10/2015 | Yarden et al. |
| 2015/0298084 A1 | 10/2015 | Schoeppe et al. |
| 2015/0299369 A1 | 10/2015 | Ausserre et al. |
| 2016/0317459 A1 | 11/2016 | Ensign et al. |
| 2016/0346266 A1 | 12/2016 | Tolleth et al. |
| 2017/0042823 A1 | 2/2017 | Prud'Homme et al. |
| 2017/0151339 A1 | 6/2017 | White et al. |
| 2017/0209386 A1 | 7/2017 | Pagels et al. |
| 2018/0125915 A1 | 5/2018 | Mikhail |
| 2019/0008788 A1 | 1/2019 | Prud'Homme et al. |
| 2019/0151252 A1 | 5/2019 | Pagels et al. |
| 2019/0192444 A1 | 6/2019 | Barzilay et al. |
| 2020/0206136 A1 | 7/2020 | Prud'Homme et al. |

FOREIGN PATENT DOCUMENTS

| | | | |
|---|---|---|---|
| CN | 102334609 A | | 2/2012 |
| CN | 104042567 A | | 9/2014 |
| CN | 105213250 A | * | 1/2016 |
| CN | 105213250 A | | 1/2016 |
| EP | 2962752 A1 | | 1/2016 |
| JP | 2003513019 A | | 4/2003 |
| JP | 2008297288 A | | 12/2008 |
| JP | 2014514275 A | | 6/2014 |
| JP | 2015129128 A | | 7/2015 |
| JP | 2015529683 A | | 10/2015 |
| JP | 2017505800 A | | 2/2017 |
| JP | 2018535228 A | | 11/2018 |
| WO | 1994008599 A1 | | 4/1994 |
| WO | 1997049736 A2 | | 12/1997 |
| WO | 2001022937 A1 | | 4/2001 |
| WO | 2002076441 A1 | | 10/2002 |
| WO | 2002078674 A1 | | 10/2002 |
| WO | 2002092069 A1 | | 11/2002 |
| WO | WO-02092069 A1 | * | 11/2002 |
| WO | 2009080164 A1 | | 7/2009 |
| WO | 2012122544 A2 | | 9/2012 |
| WO | 2013023003 A1 | | 2/2013 |
| WO | 2013160773 A2 | | 10/2013 |
| WO | 2014043625 A1 | | 3/2014 |
| WO | 2014133172 A1 | | 9/2014 |
| WO | 2014165679 A1 | | 10/2014 |
| WO | 2015123562 A1 | | 8/2015 |
| WO | 2015130835 A1 | | 9/2015 |
| WO | 2015200054 A2 | | 12/2015 |
| WO | 2015200054 A9 | | 12/2015 |
| WO | WO-2016193810 A1 | * | 12/2016 ............ A61K 38/13 |
| WO | 2017089942 A1 | | 6/2017 |
| WO | 2017112828 A1 | | 6/2017 |
| WO | 2017130046 A1 | | 8/2017 |
| WO | WO-2017130046 A1 | * | 8/2017 |
| WO | 2019050969 A1 | | 3/2019 |
| WO | 2019055539 A1 | | 3/2019 |
| WO | WO-2019050969 A1 | * | 3/2019 |
| WO | 2019090030 A1 | | 5/2019 |
| WO | 2020018890 A1 | | 1/2020 |
| WO | 2020252346 A1 | | 12/2020 |
| WO | WO-2020252346 A1 | * | 12/2020 |

OTHER PUBLICATIONS

Xtend-life.com, "Enteric Coating—The Enteric Coating Process", downloaded from web page: https://www.extend-life.com/pages/enteric-coating, download date: Apr. 6, 2023, original posting date: unknown, 6 pages. (Year: 2023).*

3uo et al., "Biosynthesis of gold nanoparticles using a kind of flavonol: Dihydromyricetin", Colloids and Surfaces A: Physicochemical and Engineering Aspects, vol. 441, pp. 127-132 (2014). (Year: 2014).*

6 International Search Report and Written Opinion dated Sep. 11, 2020 in International Application No. PCT/US2020/037542. (Year: 2020).*

Sheela et al., "Laurie acid induce cell death in colon cancer cells mediated by the epidermal growth factor receptor downregulalion: An in silico and in vitro study", Human and Experimental Toxicology, pp. 1-9 (Apr. 3, 2019). (Year: 2019).*

Smith, J., "The Complete Guide to Enteric Coating", ASTEnzymes. com, Aug. 15, 2018, downloaded from web page: https://astenzymes.com/lhe-complele-guide-lo-enleric-coaling/, download date: Apr. 6, 2023, original post date: unknown, 11 pages. (Year: 2018).*

U.S. Appl. No. 16/810,710 Office Action dated Mar. 30, 2022. (Year: 2022).*

U.S. Appl. No. 16/810,710 Requirement for Restriction/Election dated Jan. 6, 2021. (Year: 2021).*

English language translation of CN-100389766-C (Year: 2008).*

English language translation of CN-105213250-A (Year: 2016).*

IQQueryQuickExport search results—202004301605 (IP.com NPL search results)—downloaded Apr. 30, 2020, 5 pages.

IQQueryQuickExport search results—202004301643 (IP.com NPL search results)—downloaded Apr. 30, 2020, 5 pages.

IQQueryQuickExport search results—202004301659 (IP.com NPL search results)—downloaded Apr. 30, 2020, 5 pages.

IQQueryQuickExport search results—202004301700 (IP.com NPL search results)—downloaded Apr. 30, 2020, 2 pages.

Jain et al., "Peptide and Protein Delivery Using New Drug Delivery Systems," Crit. Rev. Ther. Drug Carrier Syst., vol. 30, No. 4, pp. 293-329 (2013).

Jang et al., "Bicontinuous Block Copolymer Morphologies Produced by Interfacially Active, Thermally Stable Nanoparticles", Macromols., vol. 44, pp. 9366-9373 (2011).

Jang et al., "Synthesis of thermally stable Au-core/Pt-shell nanoparticles and their segregation behavior in diblock copolymer mixtures", Soft Matter, vol. 7, pp. 6255-6263 (2011), doi: 10.1039/clsm05223c.

Jeon et al., "Cooperative Assembly of Block Copolymers with Deformable Interfaces: Toward Nanostructured Particles", Advanced Materials, vol. 20, pp. 4103-4108 (2008), doi: 10.1002/adma.200801377.

Johnson et al., "Characterization and Suitability of Therapeutic Antibody Dense Phases for Subcutaneous Delivery", Molecular Pharmaceutics, vol. 10, pp. 3582-3591 (2013).

Johnson et al., "Chemical Processing and Micromixing in Confined Impinging Jets", AIChE Journal, vol. 49, No. 9, pp. 2264-2282 (2003).

Johnson et al., "Flash NanoPrecipitation of Organic Actives and Block Copolymers using a Confined Impinging Jets Mixer," Australian Journal of Chemistry, vol. 56, No. 10, pp. 1021-1024 (2003).

Johnson et al., "Nanoprecipitation of organic actives using mixing and block copolymer stabilization", Abstracts of Papers of the American Chemical Society, No. 186 (Abstract) (Sep. 2003).

(56) References Cited

OTHER PUBLICATIONS

Johnston et al., "Concentrated Dispersions of Equilibrium Protein Nanoclusters That Reversibly Dissociate into Active Monomers", ACS Nano, vol. 6, No. 2, pp. 1357-1369 (2012).
Kakizawa et al., "Controlled release of protein drugs from newly developed amphiphilic polymer-based microparticles composed of nanoparticles", Journal of Controlled Release, vol. 142, pp. 8-13 (2010).
Kang et al., "Pore Closing and Opening in Biodegradable Polymers and Their Effect on the Controlled Release of Proteins", Mol. Pharmaceutics, vol. 4, No. 1, pp. 104-118 (2007).
Khanvilkar et al., "Drug transfer through mucus," Advanced Drug Delivery Reviews, vol. 48, Nos. 2-3, pp. 173-193 (2001).
Kim et al., "Critical effect of freezing/freeze-drying on sustained release of FITC-dextran encapsulated within PLGA microspheres", Int'l J. Pharmaceutics, vol. 271, pp. 207-214 (2004).
Kim et al., "Multicomponent Nanoparticles via Self-Assembly with Cross-Linked Block Copolymer Surfactants," angmuir, vol. 23, pp. 2198-2202 (2007).
Kohen, N., "Characterization of Polystyrene-block-poly(acrylic acid) Micelles In Solution and Assembled on Solid Substrates," Massachusetts Institute of Technology, Thesis, Jun. 2005, pp. 1-38 (2005).
Kovalainen et al., "Novel Delivery Systems for Improving the Clinical Use of Peptides", Pharmacol. Rev., vol. 67, No. 3, pp. 541-561 (Jul. 2015).
Kumar et al., "Amphiphilic Janus particles at fluid interfaces", Soft Matter, vol. 9, pp. 6604-6617 (2013).
Lai et al., "Mucus-penetrating nanoparticles for drug and gene delivery to mucosal tissues," Advanced Drug Delivery Reviews, vol. 61, No. 2, pp. 158-171 (2009).
Lai et al., "Rapid transport of large polymeric nanoparticles in fresh undiluted human mucus," Proceedings of the National Academy of Sciences, vol. 104, No. 5, pp. 1482-1487 (2007).
Langer, R., "Drug delivery and targeting," Nature, vol. 392, No. 6679, pp. 5-10 (1998).
Lavasanifar et al., "Poly(ethylene oxide)- block-poly(L-amino acid) micelles for drug delivery", Advanced Drug Delivery Reviews, vol. 54, pp. 169-190 (2002).
Li et al., "Pharmacokinetics and Biodistribution of Nanoparticles," Molecular Pharmaceutics, vol. 5, No. 4, pp. 496-504 (2008).
Liang et al., "Preparation of nanoparticles composed of poly(gamma-glutamic acid)-poly(lactide) block copolymers and evaluation of their uptake by HepG2 cells," J. Controlled Release, vol. 105, pp. 213-225 (2005).
Liu et al., "CFD Predictions for Chemical Processing in a Confined Impinging-Jets Reactor", AIChE Journal, vol. 52, No. 2, pp. 731-744 (Feb. 2006).
Liu et al., "Janus Colloids Formed by Biphasic Grafting at a Pickering Emulsion Interface", Angew. Chem., vol. 120, pp. 4037-4039 (2008).
Liu et al., "Mixing in a multi-inlet vortex mixer (MIVM) for flash nano-precipitation", Chemical Engineering Science, vol. 63, pp. 2829-2842 (2008).
Liu et al., "Ostwald ripening of beta-carotene nanoparticles", Phys. Rev. Lett., vol. 98, No. 3, pp. 036102-1-036102-4 (2007).
Livraghi et al., "Cystic Fibrosis and Other Respiratory Diseases of Impaired Mucus Clearance," Toxicologic Pathology, vol. 35, No. 1, pp. 116-129 (2007).
Lu et al., "Hydrophobic Ion Pairing of Peptide Antibiotics for Processing into Controlled Release Nanocarrier Formulations", Molecular Pharmaceutics, vol. 15, No. 1, pp. 216-225 (2018).
Luo et al., "Synthetic DNA delivery systems," Nature Biotechnology, vol. 18, No. 1, pp. 33-37 (2000).
Mai et al., "Controlled Incorporation of Particles into the Central Portion of Vesicle Walls", J. Am. Chem. Soc., vol. 132, pp. 10078-10084 (2010).
Marcus et al., "Ion Pairing," Chemical Reviews, vol. 106, No. 11, pp. 4585-4621 (2006).
Markwalter et al., "Inverse Flash NanoPrecipitation for Biologics Encapsulation: Understanding Process Losses via an Extraction Protocol", Control of Amphiphile Self-Assembling at the Molecular Level: Supra-Molecular Assemblies with Tuned Physicochemical Properties for Delivery Applications, pp. 275-296 (Jan. 1, 2017).
Matschiner et al., "Optimization of topical erythromycin formulations by ion pairing," Skin Pharmacology: The Official Journal of the Skin Pharmacology Society, vol. 8, No. 6, pp. 319-325 (1995).
Meyer et al. "Hydrophobic Ion Pairing: Altering the Solubility Properties of Biomolecules," Pharmaceutical Research, vol. 15, No. 2, pp. 188-193 (1998).
Mitragotri et al. "Overcoming the challenges in administering biopharmaceuticals: formulation and delivery strategies", Nat. Rev. Drug Discov., vol. 13, No. 9, pp. 655-672 (Sep. 2014).
Muehle et al., "Stability of Particle Aggregates in Flocculation with Polymers: Stabilität von Teilchenaggregaten bei der Flockung mit Polymeren", Chemical Engineering and Processing: Process Intensification, vol. 29, No. 1, pp. 1-8 (1991).
Mueller et al., "Solid lipid nanoparticles (SLN) for controlled drug delivery-a review of the state of the art," European Journal of Pharmaceutics and Biopharmaceutics, vol. 50, No. 1, pp. 161-177 (2000).
Muheem et al., "A review on the strategies for oral delivery of proteins and peptides and their clinical perspectives," Saudi Pharmaceutical Journal, vol. 24, No. 4, pp. 413-428 (2016).
Notice of Allowance dated Apr. 12, 2022 in U.S. Appl. No. 16/253,850.
O'Reilly et al., "Cross-linked block copolymer micelles: functional nanostructures of great potential and versatility", Chemical Society Reviews, vol. 35, pp. 1068-1083 (2006).
Okuyama et al., "Preparation of functional nanostructured particles by spray drying", Advanced Powder Technol., vol. 17, No. 6, pp. 587-611 (2006).
Overbeek et al., "Phase separation in polyelectrolyte solutions. Theory of complex coacervation," Journal of Cellular Physiology, vol. 49, No. S1, pp. 7-26 (1957).
Owens et al., "Opsonization, biodistribution, and pharmacokinetics of polymeric nanoparticles," International Journal of Pharmaceutics, vol. 307, No. 1, pp. 93-102 (2006).
Pagels et al., "Inverse Flash NanoPrecipitation for Biologics Encapsulation: Nanoparticle Formation and Ionic Stabilization in Organic Solvents", ACS Publications, vol. 1271, pp. 249-274, 2017.
Pagels et al., "Polymeric nanoparticles and microparticles for the delivery of peptides, biologics, and soluble therapeutics," Journal of Controlled Release, vol. 219, pp. 519-535 (2015).
U.S. Appl. No. 16/517,510 Office Action dated Sep. 2, 20214.
U.S. Appl. No. 16/761,140 Office Action dated Feb. 8, 2022.
U.S. Appl. No. 16/761,140 Office Action dated Aug. 26, 2022.
U.S. Appl. No. 16/761,140 Restriction Requirement dated Aug. 19, 2021.
U.S. Appl. No. 16/816,241 Office Action dated May 12, 2022.
U.S. Appl. No. 16/816,241 Restriction Requirement dated Sep. 30, 2021.
Vyavahare et al., "Analysis of Structural Rearrangements of Poly(lactic acid) in the Presence of Water", The Journal of Physical Chemistry B, vol. 118, No. 15, pp. 4185-4193 (2014).
Wang et al., "Characterization of the initial burst release of a model peptide from poly(D,L-lactide-co-glycolide) microspheres", J. Controlled Release, vol. 82, pp. 289-307 (2002).
Xu et al., "Scalable method to produce biodegradable nanoparticles that rapidly penetrate human mucus", Journal of Controlled Release, vol. 170, pp. 279-286 (2013).
Yu et al., "Nanotechnology for Protein Delivery: Overview and Perspectives", J. Control. Release, vol. 240, pp. 24-37 (2016).
Zandonella, "Bob Prud'homme—Flash NanoPrecipitation" http://research.princeton.edu/news/features/a/index.XML?d=6234, accessed Mar. 9, 2018, originally published Dec. 9, 2011, 2 printed pages.
Zhang et al., "Amphiphilic cylindrical brushes with poly(acrylic acid) core and poly(n-butyl acrylate) shell and narrow ength distribution", Polymer, vol. 44, pp. 1449-1458 (2003).
Zhang et al., "Development of Nanoparticles for Antimicrobial Drug Delivery" Current Medicinal Chemistry, vol. 17, No. 6, pp. 585-594 (2010).
Zhu et al., "Preparation and characterization of hCG-loaded polylactide or poly(lactide-co-glycolide) microspheres using a modified water-

(56) References Cited

OTHER PUBLICATIONS in-oil-in-water (w/o/w) emulsion solvent evaporation technique," J. Microencapsulation, vol. 18, No. 2, pp. 247-260 (2001).
Aggarwal et al., "What's fueling the biotech engine—2012 to 2013", Nat. Biotechnol., vol. 32, No. 1, pp. 32-39, Jan. 2014.
Ansell et al., "Modulating the Therapeutic Activity of Nanoparticle Delivered Paclitaxel by Manipulating the Hydrophobicity of Prodrug Conjugates," Journal of Medicinal Chemistry, vol. 51, No. 11, pp. 3288-3296 (2008).
Anton et al., "Aqueous-Core Lipid Nanocapsules for Encapsulating Fragile Hydrophilic and/or Lipophilic Molecules," Langmuir, vol. 25, No. 19, pp. 11413-11419 (2009).
Antonietti et al., "Polyelectrolyte-Surfactant Complexes: A New Type of Solid, Mesomorphous Material," Macromolecules, vol. 27, No. 21, pp. 6007-6011 (1994).
Antonov et al., "Entering and exiting the protein?polyelectrolyte coacervate phase via nonmonotonic salt dependence of critical conditions," Biomacromolecules, vol. 11, No. 1, pp. 51-59 (2009).
Arshady, "Preparation of biodegradable microspheres and microcapsules: 2. Polyactides and related polyesters", Journal of Controlled Release, vol. 17, pp. 1-22, (1991).
Bilati et al., "Development of a nanoprecipitation method intended for the entrapment of hydrophilic drugs into nanoparticles", European J. Pharmaceutical Sciences, vol. 24, pp. 67-75 (2005).
Bilati et al., "Nanoprecipitation Versus Emulsion-based Techniques for the Encapsulation of Proteins Into Biodegradable Nanoparticles and Process-related Stability Issues", AAPS PharmSciTech, vol. 6, No. 4, Article 74, pp. E594-E604 (2005).
Bontha et al., "Polymer micelles with cross-linked ionic cores for delivery of anticancer drugs", Journal of Controlled Release, vol. 114, pp. 163-174 (2006).
Bronich et al., "Polymer Micelle with Cross-Linked Ionic Core", J. Am. Chem Soc., vol. 127, pp. 8236-8237 (2005).
Bronich et al., "Soluble Complexes from Poly(ethylene oxide)-block-polymethacrylate Anions and N-Alkylpyridinium Cations", Macromolecules, vol. 30, pp. 3519-3525 (1997).
Bruno et al., Basics and recent advances in peptide and protein drug delivery, Therapeutic Delivery, vol. 4, No. 11,opp. 1443-1467 (2013).
Colombani et al., "Structure of Micelles of Poly(n-butyl acrylate)-block-poly(acrylic acid) Diblock Copolymers in Aqueous Solution," Macromolecules, vol. 40, pp. 4351-4362 (2007).
Colombani et al., "Synthesis of Poly(n-butyl acrylate)-block-poly(acrylic acid) Diblock Copolymers by ATRP and Their Micellization in Water," Macromolecules, vol. 40, pp. 4338-4350 (2007).
Crater et al., "Barrier Properties of Gastrointestinal Mucus to Nanoparticle Transport," Macromolecular Bioscience, vol. 10, No. 12, pp. 1473-1483 (2010).
Cu et al., "Drug delivery: Stealth particles give mucus the slip," Nature Materials, vol. 8, No. 1, pp. 11-13 (2009).
D'Addio et al., "Controlling drug nanoparticle formation by rapid precipitation", Advanced Drug Delivery Reviews, vol. 63, pp. 417-426 (2011).
Davies et al., "Recent advances in the management of cystic fibrosis," Archives of Disease in Childhood, vol. 99, No. 11, pp. 1033-1036 (2014).
Deng et al., "Janus Nanoparticles of Block Copolymers by Emulsion Solvent Evaporation Induced Assembly," Macromolecules, vol. 49, pp. 1362-1368 (2016).
Eghbali et al., "Rheology and Phase Behavior of Poly(n-butyl acrylate)-block-poly(acrylic acid) in Aqueous Solution," angmuir, vol. 22, pp. 4766-4776 (2006).
Ensign et al., "Oral drug delivery with polymeric nanoparticles: The gastrointestinal mucus barriers," Advanced Drug Delivery Reviews, vol. 64, No. 6, pp. 557-570 (2012).
Erre et al., "Chromium(III) Acetate, Chromium(III) Acetate Hydroxide, or m3-Oxo-esakis-(m2-acetato-O,O')-triaqua-trichromium(III) Acetate?" Journal of Chemical Education, vol. 74, No. 4, pp. 432-435 (1997).

Extended European Search Report (EESR) dated Jan. 8, 2018 in European Application No. 15811879.4.
Foerster et al., "Amphiphilic Block Copolymers in Structure-Controlled Nanomaterial Hybrids", Advanced Materials, vol. 10, No. 3, pp. 195-217 (1998).
Galindo-Rodriguez et al., "Polymeric nanoparticles for oral delivery of drugs and vaccines: a critical evaluation of in vivo studies," Critical Reviews in Therapeutic Drug Carrier Systems, vol. 22, No. 5, pp. 419-464 (2005).
Gao et al., "Core Cross-Linked Reverse Micelles from Star-Shaped Polymers," Chemistry of Materials, vol. 20, pp. 3063-3067 (2008).
Gaudana et al., "Design and evaluation of a novel nanoparticulate-based formulation encapsulating a HIP complex of lysozyme," Pharmaceutical Development and Technology, vol. 18, No. 3, pp. 752-759 (2013).
Gindy et al., "Mechanism of macromolecular structure evolution in self-assembled lipid nanoparticles for siRNA delivery," Langmuir, vol. 30, No. 16, pp. 4613-4622 (2014).
Google Scholar NPL search string—downloaded Apr. 29, 2020, 1 page.
Gregory et al., "Adsorption and flocculation by polymers and polymer mixtures", Advances in Colloid and Interface Science, vol. 169, No. 1, pp. 1-12 (2011).
Groeschel et al., "Guided hierarchical co-assembly of soft patchy nanoparticles", Nature, vol. 503, pp. 247-251 (5 pages & 11 pages Methods, Extended Data Figures 1-9, & Extended Data Table 1) (Nov. 14, 2013).
Guo et al., "Binding of dihydromyricetin and its metal ion complexes with bovine serum albumin", Biotechnology & Biotechnological Equipment, vol. 28, No. 2, pp. 333-341 (2014).
Guo et al., "Synthesis of dihydromyricetin-manganese (II) complex and interaction with DNA", J. Molecular Structure, vol. 1027, pp. 64-69 (2012).
Holland et al., "Polymers for Biodegradable Medical Devices, 1. The Potential of Polyesters As Controlled by Macromolecular Release Systems", Journal of Controlled Release, vol. 4, pp. 155-180 (1986).
Horigome, et al., "Long-Time Relaxation of Suspensions Flocculated by Associating Polymers", Langmuir, vol. 18, No. 6, pp. 1968-1973 (2002).
Høiby, "Recent advances in the treatment of Pseudomonas aeruginosa infections in cystic fibrosis", BMC Medicine, vol. 9, No. 32, pp. 1-7 (2011).
Ilton et al., "Direct Measurement of the Critical Pore Size in a Model Membrane", Physical Review Letters, 117, Issue 25, Dec. 2016.
Immordino et al., "Stealth liposomes: review of the basic science, rationale, and clinical applications, existing and potential," International Journal of Nanomedicine, vol. 1, No. 3, pp. 297-315 (2006).
Int'l Search Report and Written Opinion dated Jul. 16, 2015 in Int'l Application No. PCT/US2015/017590.
Int'l Search Report and Written Opinion dated Sep. 18, 2015 in Int'l Application PCT/US2015/036060.
Int'l Search Report and Written Opinion dated Mar. 23, 2017 in Int'l Application No. PCT/US2016/068145.
Int'l Search Report and Written Opinion dated Jan. 26, 2018 in Int'l Application No. PCT/US2017/054779.
International Preliminary Report on Patentability dated Mar. 26, 2020 (dated Mar. 17, 2020) in International Application No. PCT/US2018/050714.
International Search Report and Written Opinion dated Dec. 6, 2018 in International Application No. PCT/US2018/050714.
International Search Report and Written Opinion dated Jan. 15, 2019 in International Application No. PCT/US2018/049580.
International Search Report and Written Opinion dated Feb. 22, 2019 in International Application No. PCT/US2018/058869.
International Search Report and Written Opinion dated Nov. 22, 2019 in International Application No. PCT/US2019/042574.
International Search Report and Written Opinion dated Jan. 26, 2018 in International Application No. PCT/US2017/054779.
IQQueryQuickExport search results—202004301516 (IP.com NPL search results)—downloaded Apr. 30, 2020, 4 pages.

(56) References Cited

OTHER PUBLICATIONS

IQQueryQuickExport search results—202004301547 (IP.com NPL search results)—downloaded Apr. 30, 2020, 2 pages.
Patel et al., "A novel approach for antibody Nanocarriers development through hydrophobic ion-pairing complexation," Journal of Microencapsulation, vol. 31, No. 6, pp. 542-550 (2014).
Patil et al., "Retention of trypsin activity in spermine alginate microcapsules", Journal of Microencapsulation, vol. 14, No. 4, pp. 469-474 (1997).
Pattni et al., "New Developments in Liposomal Drug Delivery," Chemical Reviews, vol. 115, No. 19, pp. 10938-10966 (2015).
Peters et al., "Biotech Products in Big Pharma Clinical Pipelines Have Grown Dramatically According to the Tufts Center for the Study of Drug Development", Nov. 14, 2013, https://www.biospace.com/ . . . a-clinical-pipelines- have-grown-dramatically-according-to-the-tufts-center-for-the-study-of-drug-development-/, accessed Aug. 29, 2018 (5 pages).
Pham et al., "Micellar Solutions of Associative Triblock Copolymers: Entropic Attraction and Gas-Liquid Transition", Macromolecules, vol. 32, No. 9, pp. 2996-3005 (1999).
Pinkerton et al., "Formation of stable nanocarriers by in situ ion pairing during block-copolymer directed rapid precipitation," Molecular Pharmaceutics, vol. 10, No. 1, pp. 319-328 (2013).
Pitt, "The controlled parenteral delivery of polypeptides and proteins", International Journal of Pharmaceutics, vol. 59, pp. 173-196 (1990).
Prud'Homme et al., "Process for Encapsulating Soluble Biologics Therapeutics, and Imaging Agents", U.S. Appl. No. 16/064,935, filed Jun. 21, 2018.
Pustulka et al., "Flash Nanoprecipitation: Particle Structure and Stability," Molecular Pharmaceutics, vol. 10, pp. 4367-4377 (2013).
Qi et al., "Determination of the Bioavailability of Biotin Conjugated onto Shell Cross-Linked (SCK) Nanoparticles," Journal of the American Chemical Society, vol. 126, pp. 6599-6607 (2004).
Reinhold et al., "Self-healing Microencapsulation of Biomacromolecules without Organic Solvents", Angew. Chem. Int. Ed. Engl., vol. 51, No. 43, pp. 10800-10803 (2012).
Reinhold et al., "Self-Healing Microencapsulation of Biomacromolecules without Organic Solvents", Angewandte Chemie, vol. 124, Issue 43, pp. 10958-10961, Oct. 2012.
Riess et al., "Emulsifying Properties of Block Copolymers. Oil-Water Emulsions and Microemulsions", Polym. Eng. Sci., vol. 17, No. 8, pp. 634-638 (1977).
Radler et al., "Structure of DNA-cationic liposome complexes: DNA intercalation in multilamellar membranes in distinct Interhelical packing regimes," Science, vol. 275, No. 5301, pp. 810-814 (1997).
Saad et al., "Principles of nanoparticle formation by Flash Nanoprecipitation", Nano Today, vol. 11, No. 2, pp. 212-227 (2016), http://dx.doi.org/10.1016/j.nantod.2016.04.006.
Sahoo et al., "Characterization of Porous PLGA/PLA Microparticles as a Scaffold for Three Dimensional Growth of Breast Cancer Cells", Biomacromolecules, vol. 6, pp. 1132-1139 (2005).
Salentinig et al., "Self-Assembled Structures and pKa Value of Oleic Acid in Systems of Biological Relevance," angmuir, vol. 26, No. 14, pp. 11670-11679 (2010). DOI: 10.1021/la101012a.
Sato et al., "Therapeutic peptides: technological advances driving peptides into development", Current Opinion in Biotechnology, vol. 17, pp. 638-642 (2006).
Schwendeman et al., "Injectable controlled release depots for large molecules", Journal of Controlled Release, vol. 190, pp. 240-253 (2014).
Serajuddin, "Salt formation to improve drug solubility" Advanced Drug Delivery Reviews, vol. 59, No. 7, pp. 603-616 (2007).
Shah et al., Poly (glycolic acid-co-DL-lactic acid): diffusion or degradation controlled drug delivery?, Journal of Controlled Release, vol. 18, pp. 261-270 (1992).
Sohn et al., "Polymer prodrug approaches applied to paclitaxel," Polymer Chemistry, vol. 1, No. 6, pp. 778-792 (2010).
Solaro et al., "Targeted Delivery of Protein Drugs by Nanocarriers", Materials, vol. 3, No. 3, pp. 1928-1980 (2010).
Song et al., "A novel in situ hydrophobic ion pairing (HIP) formulation strategy for clinical product selection of a hanoparticle drug delivery system," Journal of Controlled Release, vol. 229, pp. 106-119 (2016).
Sosa et al., "Soft Multifaced and Patchy Colloids by Constrained vol. Self-Assembly", Macromolecules, vol. 49, pp. 3580-3585 (2016).
Steichen et al., "A review of current nanoparticle and targeting moieties for the delivery of cancer therapeutics", European J. Pharmaceutical Sciences, vol. 48, pp. 416-427 (2013).
Talelli et al., "Core-crosslinked polymeric micelles: Principles, preparation, biomedical applications and clinical translation," Nano Today, vol. 10, pp. 93-117 (2015).
Tang et al., "An innovative method for preparation of hydrophobic ion-pairing colistin entrapped poly(lactic acid) nanoparticles: Loading and release mechanism study", European J. Pharmaceutical Sciences, vol. 102, pp. 63-70 (2017).
Turro et al., "Spectroscopic probe analysis of protein-surfactant interactions: the BSA/SDS system," Langmuir, vol. 11, No. 7, pp. 2525-2533 (1995).
U.S. Appl. No. 16/517,510 Notice of Allowance dated May 9, 2022.
U.S. Appl. No. 16/517,510 Restriction Requirement dated Mar. 19, 2021.
U.S. Patent & Trademark Office (USPTO) Communication dated Mar. 9, 2021 for U.S. Appl. No. 16/253,850.
U.S. Patent & Trademark Office (USPTO) Office Action dated May 12, 2021 for U.S. Appl. No. 16/810,710.
U.S. Patent & Trademark Office (USPTO) Office Action dated Sep. 23, 2021 for U.S. Appl. No. 16/253,850.
U.S. Appl. No. 15/321,588 Notice of Allowance dated Oct. 24, 2018.
U.S. Appl. No. 15/321,588 Office Action dated Apr. 10, 2018.
U.S. Appl. No. 15/321,588 Restriction Requirement dated Dec. 1, 2017.
U.S. Appl. No. 15/321,588 Summary of Examiner Interview dated Oct. 9, 2018.
U.S. Appl. No. 16/064,935 Notice of Allowance dated Aug. 2, 2021.
U.S. Appl. No. 16/064,935 Notice of Allowance dated Jun. 21, 2021.
U.S. Appl. No. 16/064,935 Notice of Allowance dated Oct. 21, 2020.
U.S. Appl. No. 16/064,935 Notice of Allowance dated Apr. 28, 2021.
U.S. Appl. No. 16/064,935 Notice of Allowance dated May 6, 2020.
U.S. Appl. No. 16/064,935 Requirement for Restriction/Election dated Jan. 13, 2020.
U.S. Appl. No. 16/253,850 Office Action dated Sep. 8, 2020.
U.S. Appl. No. 16/253,850 Restriction Requirement dated Apr. 7, 2020.
U.S. Appl. No. 16/517,510 Notice of Allowance and Notice of Allowability dated Nov. 23, 2022.
U.S. Appl. No. 16/816,241 Notice of Allowance and Notice of Allowability dated Nov. 16, 2022.
U.S. Appl. No. 16/253,850, filed Aug. 11, 2021 dated Summary of Interview dated Aug. 9, 2021.
U.S. Appl. No. 16/253,850 Notice of Allowance dated Sep. 13, 2022.
Babu et al., "Solubility Advantage of Amorphous Drugs and Pharmaceutical Cocrystals", Crystal Growth & Design, vol. 11, pp. 2662-2679 (2011).
Bailly et al., "Poly(N-vinylpyrrolidone)-block-poly(vinyl acetate) as a Drug Delivery Vehicle for Hydrophobic Drugs", vol. 13, pp. 4109-4117 (Nov. 2, 2012).
Etchenausia et al., "RAFT/MADIX emulsion copolymerization of vinyl acetate and N-vinylcaprolactam: towards waterborne physically crosslinked thermoresponsive particles", Polymer Chemistry, pp. 1-28 (2017).
xtend-life.com, "Enteric Coating—The Enteric Coating Process", downloaded from web page: https://www.extend-life.com/pages/enteric-coating, download date: Aug. 12, 2020, original posting date: unknown, 6 pages.

(56) References Cited

OTHER PUBLICATIONS

Guo et al., "Biosynthesis of gold nanoparticles using a kind of flavonol: Dihydromyricetin", Colloids and Surfaces A: Physicochemical and Engineering Aspects, vol. 441, pp. 127-132 (2014).
International Search Report and Written Opinion dated Sep. 11, 2020 in International Application No. PCT/US2020/037542.
Sheela et al., "Lauric acid induce cell death in colon cancer cells mediated by the epidermal growth factor receptor downregulation: An in silico and in vitro study", Human and Experimental Toxicology, pp. 1-9 (Apr. 3, 2019).
Smith, J., "The Complete Guide to Enteric Coating", ASTEnzymes. com, Aug. 15, 2018, downloaded from web page: https://astenzymes.com/the-complete-guide-to-enteric-coating/, download date: Aug. 11, 2020, original post date: unknown, 11 pages.
U.S. Appl. No. 16/810,710 Office Action dated Mar. 30, 2022.
U.S. Appl. No. 16/810,710 Requirement for Restriction/Election dated Jan. 6, 2021.

* cited by examiner

CELLULOSIC POLYMER NANOPARTICLES AND METHODS OF FORMING THEM

This application is a continuation of International Application No. PCT/US2018/050714, filed Sep. 12, 2018, which claims the benefit of U.S. Provisional Application No. 62/557,744, filed Sep. 12, 2017, all of which are hereby incorporated by reference in its entireties herein.

FIELD OF THE INVENTION

The present invention pertains to nanoparticles including a cellulosic polymer and a hydrophobic material and methods of their formation.

SUMMARY

In an embodiment according to the invention, a nanoparticle includes a cellulosic polymer (such as a cellulosic polymer substituted with hydrophilic groups), and a hydrophobic material (an active). The cellulosic polymer can have a molecular weight of from about 10,000 to about 2,000,000 g/mol (Da), and the nanoparticle can have a size (e.g., a diameter or a mean diameter) of from about 10 nm to about 5000 nm. For example, a cellulosic polymer included in a nanoparticle according to the invention can have a molecular weight of from about 10,000 to about 2,000,000 g/mol, from about 20,000 to about 2,000,000 g/mol, from about 10,000 to about 500,000 g/mol, from about 20,000 to about 400,000 g/mol, or from about 50,000 to about 260,000 g/mol. The cellulosic polymer can have a molecular weight of from about 10,000, 20,000, 50,000, 100,000, 200,000, 250,000, 260,000, 400,000, 500,000, or 1,000,000 g/mol to about 20,000, 50,000, 100,000, 200,000, 250,000, 260,000, 400,000, 500,000, 1,000,000, or 2,000,000 g/mol. For example, a nanoparticle according to the invention can have a size (for example, a diameter, e.g., a mean diameter) of from about 10 nm to about 5000 nm, from about 20 nm to about 700 nm, from about 20 nm to about 500 nm, from about 70 nm to about 160 nm, from about 70 nm to about 100 nm, from about 100 to about 400 nm, from about 100 to about 250 nm, from about 135 nm to about 260 nm, from about 150 to about 160 nm, from about 200 to about 260 nm, or about 310 nm. The nanoparticle can have a size, e.g., a mean diameter, of from about 10, 20, 35, 50, 70, 100, 135, 150, 160, 200, 250, 260, 350, 500, 600, 700, 1000, or 2000 nm to about 20, 35, 50, 70, 100, 135, 150, 160, 200, 250, 260, 350, 500, 600, 700, 1000, 2000, or 5000 nm.

For example, the cellulosic polymer can be hydroxypropyl cellulose, methyl cellulose, ethyl methyl cellulose, hydroxypropylmethyl cellulose (HPMC), carboxymethyl cellulose, or a combination of these. The cellulosic polymer can include hydroxypropyl, hydroxyethyl, hydroxymethyl, succinate, and/or acetate substitution(s).

For example, the cellulosic polymer can be hydroxypropylmethyl cellulose including a hydroxypropyl substitution level of from about 5 to about 10% wt. For example, the cellulosic polymer can be hydroxypropylmethyl cellulose including a methoxyl substitution level of from about 20 to about 26% wt. For example, the cellulosic polymer can be hydroxypropylmethyl cellulose including an acetyl substitution level of from about 5 to about 14% wt or from about 10 to about 14% wt. For example, the cellulosic polymer can be hydroxypropylmethyl cellulose including a succinyl substitution level of from about 4 to about 18% wt or from about 4 to about 8% wt.

In an embodiment according to the invention, a nanoparticle of size of from about 20 nm to about 500 nm includes a cellulosic polymer of from about 20,000 to about 2,000,000 g/mol including a hydroxypropyl substitution level of from about 5 to about 10% wt, a methoxyl substitution level of from about 20 to about 26% wt, an acetyl substitution level of from about 5 to about 14% wt or from about 10 to about 14% wt, and a succinyl substitution level of from about 4 to about 18% wt or from 4 to about 8% wt.

For example, the nanoparticle can have a core of at most about 50% of a solvent phase.

In an embodiment according to the invention, the nanoparticle size does not change by more than about 50% over about 4 hours in aqueous solution.

For example, the hydrophobic material can have a molecular weight of from about 100, 200, 400, 500, 600, 700, 800, 1000, 1200, 1500, 2000, or 3000 g/mol to about 200, 400, 500, 600, 700, 800, 1000, 1200, 1500, 2000, 3000 or 5000 g/mol. For example, the hydrophobic material can have a solubility in water of from about 0.001, 0.003, 0.01, 0.03, 0.1, 0.2, 0.5, 1, 2, 5, 10, 20, or 50 mg/L to about 0.003, 0.01, 0.03, 0.1, 0.2, 0.5, 1, 2, 5, 10, 20, 50, or 100 mg/L. For example, the hydrophobic material can have a log P of from about 3.5, 4, 4.5, 5, 5.5, 6, 6.5, 7, 7.5, 8, 8.5, 9, 10, or 11 to about 4, 4.5, 5, 5.5, 6, 6.5, 7, 7.5, 8, 8.5, 9, 10, 11, or 12. For example, the hydrophobic material can be clofazimine, lumefantrine, cyclosporine A, itraconazole, artefenomel, artefenomel mesylate, tocopheryl, tocopheryl acetate, or combinations.

In an embodiment, a dispersion of nanoparticles according to the invention is not an emulsion.

In an embodiment, the hydrophobic material itself is a hydrophobic nanoparticle, the hydrophobic nanoparticle having a surface that is hydrophobic. For example, the hydrophobic nanoparticle can have a diameter, e.g., a mean diameter, of from about 30 nm to 400 nm, from about 40 to about 200 nm, from about 60 nm to about 150 nm, or from about 60 nm to about 125 nm. The hydrophobic nanoparticle can include a hydrophilic core, which can be crosslinked. The hydrophobic nanoparticle can include an amphiphilic copolymer, i.e., a copolymer having both hydrophilic and hydrophobic functionality or characteristics. The hydrophobic nanoparticle can include a copolymer having a hydrophobic block and a hydrophilic block; for example, the hydrophobic nanoparticle can include a triblock copolymer having a hydrophobic center block and two hydrophilic outer blocks, such as poly(aspartic acid)-b-poly(lactic acid)-b-poly(aspartic acid). For example, the hydrophobic block of the copolymer of the hydrophobic nanoparticle can have a molecular weight of from about 5 kDa (5 kg/mol) to about 40 kDa or from about 10 kDa to about 20 kDa. For example, the hydrophilic block of the copolymer of the hydrophobic nanoparticle can have a molecular weight of from about 2 kDa (kg/mol) to about 20 kDa or from about 5 kDa to about 10 kDa. The hydrophobic nanoparticle can include a hydrophilic molecule, e.g., a hydrophilic molecule having a molecular weight ranging from about 100 g/mol to about 40,000 g/mol, from about 200 g/mol to about 1500 g/mol, from about 1000 g/mol to about 40,000 g/mol, from about 5000 g/mol to about 40,000 g/mol, or from about 5000 g/mol to about 25,000 g/mol. Examples of such a hydrophilic molecule include vancomycin and lysozyme and combinations.

In a process (method) according to the invention, a nanoparticle is formed by dissolving a cellulosic polymer (such as a cellulosic polymer substituted with hydrophilic groups) in a less polar solvent to form a process solution, and combining the process solution with a more polar solvent to rapidly form or precipitate the nanoparticle. A hydrophobic material can be dissolved in the less polar solvent. The formed nanoparticle can include the cellulosic polymer and the hydrophobic material. The nanoparticle can include an exterior hydrophilic shell, i.e., the nanoparticle can present a hydrophilic surface to the environment, the exterior hydrophilic shell can include the cellulosic polymer, and the exterior hydrophilic shell can surround the hydrophobic material. For example, the process solution can be in a process stream, the more polar solvent can be in a more polar solvent stream, the process stream can be continuously combined with the more polar solvent stream in a confined mixing volume, and/or the formed nanoparticle can exit the confined mixing volume in an exit stream. For example, the process stream can be continuously combined with the more polar solvent stream in a Confined Impinging Jet (CIJ) mixer or a Multi-Inlet Vortex Mixer (MIVM). For example, the less polar solvent can be an organic solvent, for example, acetone, an alcohol, methanol, ethanol, n-propanol, isopropanol, tetrahydrofuran, or combinations. For example, the more polar solvent can be water, an alcohol, or a water/alcohol combination. For example, the nanoparticle formed can have a size of from about 20 nm to about 500 nm. The cellulosic polymer can be of a hydroxypropyl substitution level of from about 5 to about 10% wt, a methoxyl substitution level of from about 20 to about 26% wt, an acetyl substitution level of from about 5 to about 14% wt or from about 10 to about 14% wt, and a succinyl substitution level of from about 4 to about 18% wt or from about 4 to about 8% wt. The molecular weight of the cellulosic polymer can be from about 20,000 to about 2,000,000 g/mol.

In a process (method) according to the invention, a nanoparticle is formed by dissolving a hydrophobic material in an organic solvent to form an organic solution, dissolving a cellulosic polymer (such as a cellulosic polymer substituted with hydrophilic groups) in an aqueous solvent to form an aqueous solution, dispersing the organic solution in the aqueous solution to form a dispersion, and removing ("stripping") the organic solvent from the dispersion to form the nanoparticle. The formed nanoparticle can include the cellulosic polymer and the hydrophobic material.

The cellulosic polymer can be of a hydroxypropyl substitution level of from about 5 to about 10% wt, a methoxyl substitution level of from about 20 to about 26% wt, an acetyl substitution level of from about 5 to about 14% wt or from about 10 to about 14% wt, and a succinyl substitution level of from about 4 to about 18% wt or from about 4 to about 8% wt. The molecular weight of the cellulosic polymer can be from about 20,000 to about 2,000,000 g/mol. The nanoparticle formed can have a size of from about 20 nm to about 500 nm.

In a process (method) according to the invention, the formed nanoparticle can be combined with a water soluble cellulosic polymer of hydroxypropyl, hydroxyethyl, hydroxymethyl, and/or methyl substitution and/or of about 20,000 to about 2,000,000 g/mol molecular weight to form a further mixture, and this further mixture can be spray dried to form a powder. The formed nanoparticle in the powder can be redispersed to within about 20%, 30%, 50%, of 100% of its original size.

In a process (method) according to the invention, the hydrophobic material (that is dissolved with the cellulosic polymer in the less polar solvent to form the process solution, and that is included with the cellulosic polymer in the nanoparticle formed) is itself a hydrophobic nanoparticle (that has a hydrophobic surface, i.e., it presents a hydrophobic surface to the environment). This hydrophobic nanoparticle can be formed by dissolving a block copolymer and a hydrophilic molecule in a preliminary polar solvent to form a preliminary polar solution and combining the preliminary polar solution with a preliminary less polar solvent to (rapidly) form a hydrophobic nanoparticle and a preliminary nanoparticle solvent (the hydrophobic nanoparticle and the preliminary nanoparticle solvent can be in a preliminary nanoparticle solution). The block copolymer can include a hydrophobic block and a hydrophilic block. The hydrophobic nanoparticle can have a hydrophilic core that includes the hydrophilic block of the block copolymer and the hydrophilic molecule. The hydrophobic nanoparticle can have a shell, including the hydrophobic surface, that includes the hydrophobic block of the copolymer. The preliminary less polar solvent can be less polar than the preliminary polar solvent.

For example, the hydrophobic nanoparticle formed can have a diameter (e.g., a mean diameter) of from 30 to 400 nm, of from 40 to 200 nm, or of from 60 to 150 nm.

For example, the block copolymer of the hydrophobic nanoparticle can include a triblock copolymer having a hydrophobic center block and two hydrophilic outer blocks. For example, the hydrophobic block can include poly(lactic acid), poly(lactic-co-glycolic acid), poly(caprolactone), or combinations. For example, the hydrophilic block can include poly(aspartic acid), poly(glutamic acid), or combinations. For example, the block copolymer can be or include poly(aspartic acid)-b-poly(lactic acid)-b-poly(aspartic acid). The preliminary polar solvent can include water and/or dimethyl sulfoxide (DMSO). The preliminary less polar solvent can include dichloromethane and/or chloroform.

For example, the hydrophilic molecule can have a molecular weight ranging from 100 g/mol to 40,000 g/mol, from 200 g/mol to 1500 g/mol, from 1000 g/mol to 40,000 g/mol, from 5000 g/mol to 40,000 g/mol, or from 5000 g/mol to 25,000 g/mol. For example, the hydrophilic molecule can include vancomycin and/or lysozyme.

The process can include adding a crosslinking agent (such as tetraethylenepentamine (TEPA)) to the preliminary nanoparticle solution to crosslink (e.g., ionically crosslink) the hydrophilic block in the hydrophilic core of the hydrophobic nanoparticle.

The process can include exchanging (swapping) the preliminary nanoparticle solvent used to form the hydrophobic nanoparticle with the less polar solvent in which the hydrophobic nanoparticle (hydrophobic material) and the cellulosic polymer are dissolved to form the process solution. For example, the preliminary nanoparticle solvent can so be exchanged (swapped) from the preliminary nanoparticle solution including the hydrophobic nanoparticle formed and the preliminary nanoparticle solvent. In the formed nanoparticle, the cellulosic polymer can encapsulate the hydrophobic nanoparticle.

DETAILED DESCRIPTION

Figure 1:
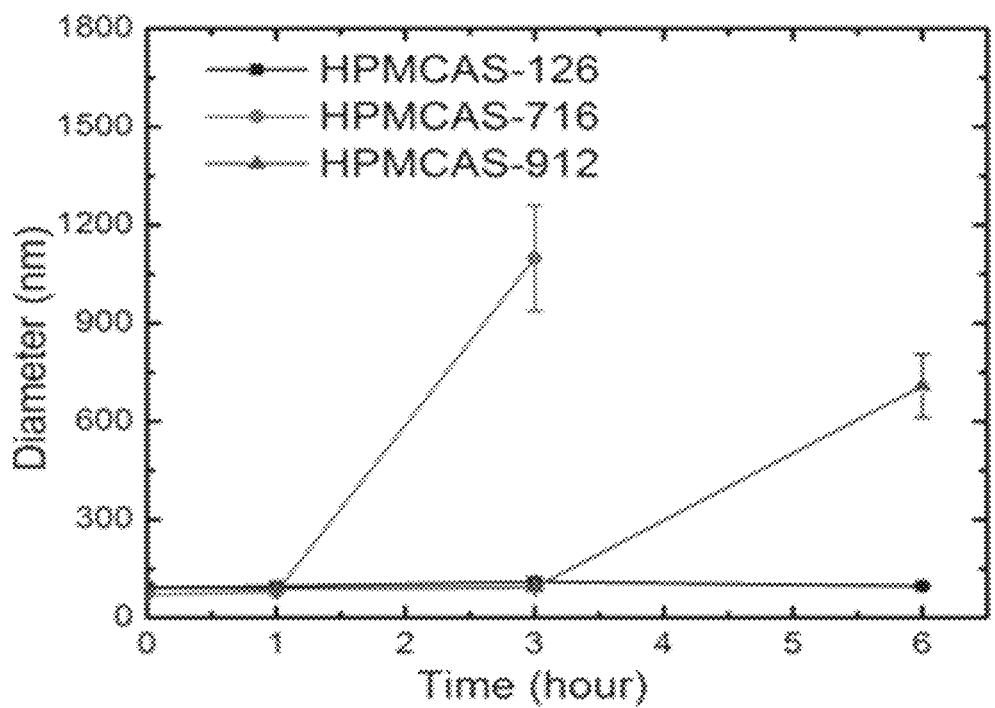
FIG. 1. Graph showing size stability over time of HPMCAS-126, HPMCAS-716, and HPMCAS-912 nanoparticles formed using mixing in a CIJ.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are hereby incorporated by reference in their entirety as if each had been individually incorporated.

Nanoparticles can be used for both parenteral and oral delivery of therapeutics and pharmaceutical agents. For external applications, nanoparticles are useful for sunscreens, cosmetics, inks, foods, flavors, fragrance applications. Nanoparticles can be applied in imaging, consumer products, and pesticide delivery.

The current invention relates to particles made from one of two processes: either rapid precipitations or emulsification followed by solvent stripping. In these operations, a stabilizing agent is required to keep the nanoparticles from aggregating. Stabilization can be achieved using polymer stabilizers. The polymers can have a hydrophobic domain to attach to a hydrophobic nanoparticle surface, and a hydrophilic domain to orient into the aqueous phase. Polymers with these characteristics are called amphiphilic polymers. The amphiphilic domains can be blocks. A block is defined as a region with either predominantly hydrophilic or predominantly hydrophobic character. Stable nanoparticles can be made using block copolymers with two distinct blocks, which are called diblock copolymers. Alternatively, nanoparticles can be made using protein stabilizers, for example, gelatin.

Nanoparticles can be made by technologies such as (1) emulsification followed by stripping and (2) polymer-directed precipitation. Emulsion-stripping technologies involve dissolving the active in an organic solvent, and dispersing the organic phase (organic solution) in an aqueous phase (aqueous solution), which can contain an emulsion stabilizer. Once the emulsion is formed, the volatile organic can be removed to create a solid particle (with the active in the core) and a surface coated with the emulsion stabilizer. (See, Hanes ("Scalable method to produce biodegradable nanoparticles that rapidly penetrate human mucus" Journal of Controlled Release 170 (2013) 279-286); and Gibson, "Emulsion-Based Processes for Making Microparticles, U.S. Pat. No. 6,291,013B1 (2001)).

Polymer-directed assembly of nanoparticles by rapid precipitations has been described by Johnson and Prud'homme, "Process and apparatuses for preparing nanoparticle compositions with amphiphilic copolymers and their use" U.S. Pat. No. 8,137,699 (2012). These polymer-directed rapid precipitations have been denoted as Flash NanoPrecipitation (FNP).

To form the nanoparticles by rapid precipitation processes, the active agents must be dissolved in a water-miscible organic solvent (the resultant organic solution is denoted "the organic stream"). Candidates for organic solvents include, but are not limited to those described in U.S. Pat. No. 8,137,699 (2012), which is hereby incorporated by reference in its entirety. Examples are methanol, ethanol, n-propanol, isopropanol, acetone, ethyl acetate, tetrahydrofuran (THF), dimethyl sulfoxide, n-methyl pyrolidone, or mixtures of these.

An aqueous solvent can be pure water, or can be water mixed with another solvent, such as an alcohol (e.g., methanol, ethanol, n-propanol, isopropanol), or a solute, such as a salt.

FNP can be performed using a mixing device such as a Confined Impinging Jet (CIJ) or a Multi-Inlet Vortex Mixer (MIVM). The CIJ used in the exemplary experiments consists of two opposed 0.5 mm jets of fluid, one organic and one aqueous, fed to a 2.4 mm diameter chamber at a constant rate with their momentum matched. The geometries of the mixers can be scaled as described by Johnson. (Also see, D'addio, S. M.; Prud'homme, R. K., Controlling drug nanoparticle formation by rapid precipitation. *Advanced drug delivery reviews* 2011, 63 (6), 417-426; and Johnson, B. K.; Prud'homme, R. K., Process and apparatuses for preparing nanoparticle compositions with amphiphilic copolymers and their use. Google Patents: 2012; and Saad, W. S.; Prud'homme, R. K., Principles of nanoparticle formation by flash nanoprecipitation. *Nano Today* 2016, 11 (2), 212-227.)

The MIVM consists of four streams and allows control of both the supersaturation and the final solvent quality by varying stream velocities. It is able to separate the reactive components into different streams prior to mixing. (See, Liu, Y.; Cheng, C. Y.; Prud'homme, R. K.; Fox, R. O., Mixing in a multi-inlet vortex mixer (MIVM) for flash nano-precipitation. *Chemical Engineering Science* 2008, 63 (11), 2829-2842.)

The FNP process is facilitated when the hydrophobic materials encapsulated into the core of nanoparticles have a log P of more than 3.5. Log P is a measure of the hydrophobicity of a compound and is defined as the logarithm of partition coefficient of the compound between octanol and water. The value can be calculated from molecular structure information by computer programs such as Mol Inspiration (Cheminformatics Inc.). Alternate techniques such as ion pairing can be used to make an active more hydrophobic so that it is amenable to rapid precipitation processes.

An embodiment of the rapid precipitation process involves the FNP process. That is, the process is conducted in a confined mixing volume with the solvent and antisolvent streams entering the confined volume, and the product stream exiting the confined volume. The precipitation is, thus, continuous; a certain total volume will be chosen to inject continuously into the confined mixing volume.

The polymeric stabilizer can be amphiphilic with distinct hydrophobic and hydrophilic blocks; the blocks can include a two-block, or di-block, copolymer.

If random polymers (e.g., random copolymers) are used, they may bridge between particles, so that stable nanoparticles are not be produced and aggregation results. That is, a steric stabilizing layer could need to have domains that hydrophobicly anchor onto the hydrophobic nanoparticle surface, and the hydrophilic domains could need to face out into the aqueous phase to provide a steric barrier to prevent particle-particle contacts. The particle bridging that occurs with inadequate distinction between hydrophilic and hydrophobic domains has been described by Pham et al. and Horigome et al. (See, Pham, Q. T., et al. "Micellar solutions of associative triblock copolymers: Entropic attraction and gas-liquid transition" *Macromolecules* 32.9 (1999): 2996-3005; and Horigome, Misao, and Yasufumi Otsubo. "Long-time relaxation of suspensions flocculated by associating polymers." *Langmuir* 18.6 (2002): 1968-1973.) Linear polymers and copolymers with random co-monomers can flocculate or aggregate particulate dispersions. (See, Halverson, Frederick. "Process for the flocculation of suspended solids." U.S. Pat. No. 4,342,653. 3 Aug. 1982; Gregory, John, and Sandor Barany. "Adsorption and flocculation by polymers and polymer mixtures." *Advances in colloid and interface science* 169.1 (2011): 1-12; and Mühle K., and K. Domasch. "Stability of particle aggregates in flocculation with polymers: Stabilität von Teilchenaggregaten bei der Flockung mit Polymeren." *Chemical Engineering and Processing: Process Intensification* 29.1 (1991): 1-8.)

Therefore, the results of the present application that randomly functionalized polymers (random cellulose copolymers) were successfully used to formulate stable nanoparticles that did not aggregate was surprising and unexpected. Not all cellulose polymers and copolymers were effective, but only those with certain functionalization, certain substitution levels, and certain compositions. Hydroxypropylmethyl cellulose (HPMC), in the class of succinic anyhydride modified cellulosics, when used as the polymeric stabilizer in Flash NanoPrecipitation, produced stable nanoparticles. Stable nanoparticles also could be formed by an emulsion-stripping processes.

The hydroxypropylmethylcellulose-acetate succinate polymers can have hydroxyproply substitution levels of 5-10% wt, methoxyl substitution levels of 20-26% wt, acetyl substitutions of 5-14% wt (such as 10-14% wt substitution), and succinyl substitutions of 4-18% wt (such as 4-8% wt). Polymers of the present invention can have weight average molecular weights of between about 10,000-2,000,000 g/mol, or about 10,000-500,000 g/mol, or about 20,000-400,000 g/mol, or about 50,000-250,000 g/mol.

It can be required that nanoparticles be put into a dry form, for example, by lyophilization, salt precipitation, or spray drying.

It was unexpectedly found that mixtures of cellulosic polymers with certain characteristics enabled spray drying of these stable cellulosic nanoparticles and their reconstitution back to nanoparticle sizes. The characteristics of the cellulosic polymers that enable spray drying without aggregation are those without succinyl substitution, such as hydroxyethlycellulose, hydroxypropyl cellulose, hydroxymethyl cellulose, and cellulosics with mixtures of these substitutions. When the nanoparticles are spray dried with cellulosics as excipients, they can be redispersed to within about 20%, 30%, 50%, or 100% of their original size. Thus, in spray drying, specific, beneficial interactions in drying the HPMC-CAS nanoparticles with a cellulosic with less hydrophobic modification was found, resulting in redispersion back into nanoparticle form. It is also possible to dry or spray dry the nanoparticle dispersion using alternative excipients in the drying, to prevent particle aggregation.

Thus, nanoparticles containing active components can be formed using specific cellulosic polymers. The particles are stable, without appreciable aggregation in solution. The nanoparticles can be produced by rapid precipitation processes or emulsion stripping processes. The resulting nanoparticles can be isolated by spray drying when a second cellulosic polymer is used in the spray drying operation.

Definitions

A nanoparticle is defined as a solid core particle with a diameter between 10-5000 nm. The size of particles between 10-600 nm can be measured by dynamic light scattering (DLS). The particles analyzed in this patent application are measured using dynamic light scattering in a Malvern Nanosizer, and the size is the z-weighted size reported using the normal mode analysis program provided by the instrument. For mode sizes between 600 and 5000 nm the size is best determined by transmission electron microscopy and is obtained by measuring on the order of 100 particles and producing a histogram.

Flash NanoPrecipitation (FNP) is a process that combines rapid micromixing in a confined geometry of miscible solvent and antisolvent streams to effect high supersaturation of components. The resulting high supersaturation results in rapid precipitation and growth of the resulting nanoparticles. A stabilizing agent in the formulation accumulates on the surface of the nanoparticle and halts growth at a desired size. The process has been described in detail in "Process and apparatuses for preparing nanoparticle compositions with amphiphilic copolymers and their use", B K Johnson, R K Prud'homme, U.S. Pat. No. 8,137,699 (2012). It has further been described in the review article by Saad and Prud'homme (see D'addio, S. M.; Prud'homme, R. K., Controlling drug nanoparticle formation by rapid precipitation. *Advanced drug delivery reviews* 2011, 63 (6), 417-426; Johnson, B. K.; Prud'homme, R. K., Process and apparatuses for preparing nanoparticle compositions with amphiphilic copolymers and their use. Google Patents: 2012; Saad, W. S.; Prud'homme, R. K., Principles of nanoparticle formation by flash nanoprecipitation. *Nano Today* 2016, 11 (2), 212-227). These references are included in this application in their entirety.

The Flash NanoPrecipitation process involves a confined mixing volume having one or more solvent streams entering the mixing volume, one or more antisolvent streams entering the mixing volume, and an exit stream (leaving the mixing volume) for the process. The velocity of the inlet streams into the confined mixing volume can be between about 0.01 m/s and 100 m/s, or about 0.1 m/s and 50 m/s, or about 0.1 m/s and 10 m/s. The velocities of the streams may be equal to one another, or they may have different velocities. In the case of unequal velocities, the velocity of the highest velocity stream is the specified velocity.

Active: An active is the component or material which confers the desired performance or result. This may be a pharmaceutical active (e.g., a drug, a therapeutic, or a diagnostic (e.g., tracing) material), a fragrance, a cosmetic, a pesticide, an herbicide, an ink or a dye, a molecule or composition that enables covert security labeling, or a molecule or composition that registers a change in color when undergoing some process event.

The term "size" can refer to a characteristic length of a nanoparticle or a hydrophobic nanoparticle. For example, the term "size" can be a diameter of a nanoparticle or a hydrophobic nanoparticle. For example, when referring to a distribution of particles, the term "size" can refer to a mean diameter of the distribution of nanoparticles or hydrophobic nanoparticles. For example, the term "size" can refer to the z-weighted size of a distribution of nanoparticles or hydrophobic nanoparticles as determined by dynamic light scattering (DLS).

EXAMPLES

HPMCAS is a cellulosic polymer of a cellulose ester bearing acetyl and succinyl groups. It is synthesized by the esterification of HPMC (hydroxypropylmethyl cellulose) with acetic anhydride and succinic anhydride, which offers flexibility in acetate and succinate substitution levels, and which allows for optimization of both solubility enhancement and material processing. HPMCAS has been used to maintain stable solid dispersions and inhibit drug crystallization through spray-dried dispersion or hot melt extrusion. However, few studies focus on developing a nanoparticle formulation with HPMCAS as the surface stabilizer. Here three HPMCAS polymers with different substitution ratios of succinyl and acetyl groups are used in Flash NanoPrecipitation of a new nanoparticle formulation. AFFINISOL™ Hypromellose acetate succinate (HPMCAS) 126, 716, 912 polymers were donated from Dow Chemical Company (Midland, Mich.). HPMCAS 126 has the highest acetyl substitution and is the most hydrophobic, and HPMCAS 716 is the most hydrophilic, with the highest succinyl substitution. In the following, several examples of successful encapsulation of a variety of active pharmaceutical ingredients with nanoparticles stabilized by HPMCAS are provided.

HPMCAS 126 can have a hydroxypropyl substitution of from about 6 to about 10%, a methoxyl substitution of from 22 to 26%, an acetate (acetyl) substitution of from about 10 to about 14%, and a succinate (succinyl) substitution of from about 4 to about 8%. HPMCAS 716 can have a hydroxypropyl substitution of from about 5 to about 9%, a methoxyl substitution of from about 20 to about 24%, an acetate (acetyl) substitution of from about 5 to about 9%, and a succinate (succinyl) substitution of from about 14 to about 18%. HPMCAS 912 can have a hydroxypropyl substitution of from about 5 to about 9%, a methoxyl substitution of from about 21 to about 25%, an acetate (acetyl) substitution of from about 7 to about 11%, and a succinate (succinyl) substitution of from about 10 to about 14%. HPMC E3 (METHOCEL E3 Dow Chemical Company) can have a hydroxypropyl substitution of from about 7 to about 12% and a methoxyl substitution of from about 28 to about 30%.

Example 1: Clofazimine-Loaded HPMCAS Nanoparticles

Clofazimine (5 mg), as well as 5 mg of the stabilizers (HPMCAS 126, 716, 912) was added to 1 mL acetone to make an organic solution. (Clofazimine has a molecular weight of 473 g/mol, solubility in water of about from 0.23 to 1.5 mg/L, and a log P of about from 7 to 7.7.) This solution was Flash NanoPrecipitated against 1 mL MilliQ water into a 9 mL reservoir of stirring MilliQ water using a CIJ mixer. DLS measurements showed that three HPMCAS polymers were able to form clofazimine loaded nanoparticles, with sizes ranging from 70 nm to 100 nm. For HPMCAS 716/912 nanoparticles, particle size increased rapidly within 3 hrs, indicating aggregation. In contrast, HPMCAS 126 nanoparticles remained at a constant size for at least 6 hours, allowing a sufficiently long enough period for later processing into dry powders. (See FIG. 1.) Hence, based on the nanoparticle stability, HPMCAS-126 nanoparticles were selected in the following discussions regarding drying.

Figure 2:
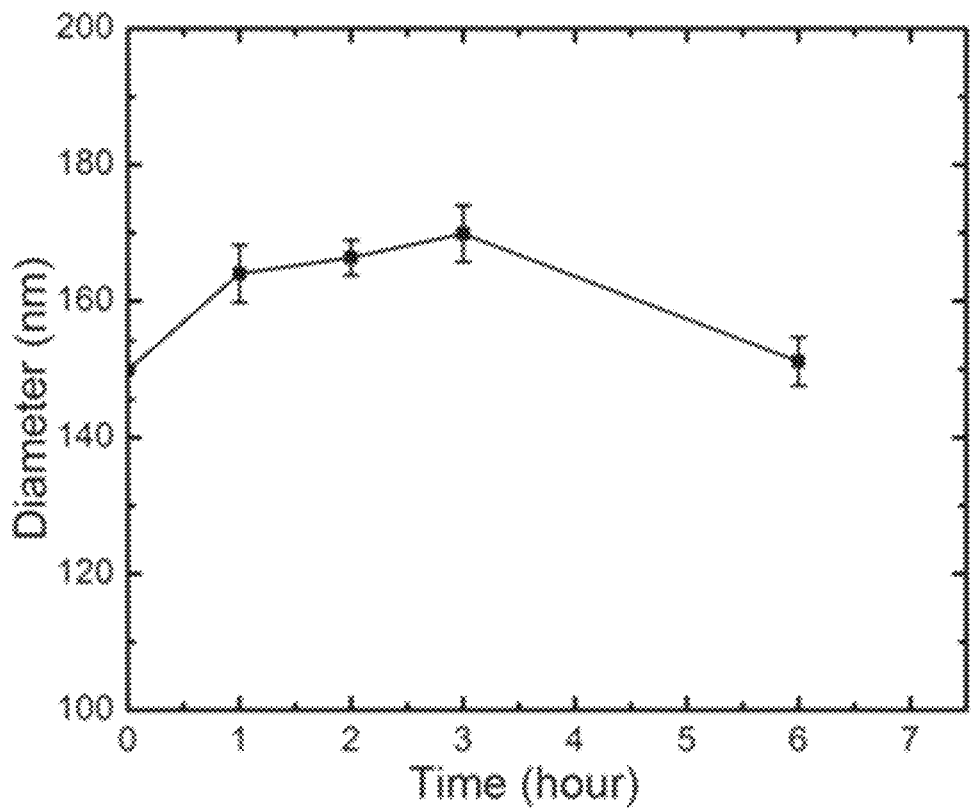
FIG. 2. Graph showing size stability of HPMCAS-126 nanoparticles using mixing in an MIVM.

Example 2: Spray-Drying and Redispersion of Clofazimine-Loaded HPMCAS Nanoparticles Clofazimine (125 mg) was added to 25 mL acetone, as well as 125 mg of HPMCAS-126. This solution was flash nanoprecipitated using a MIVM, where the acetone solution was pumped at 16 mL/min against three separate MilliQ water streams, each being pumped at 48 mL/min, for a 9:1 water:acetone ratio. The resulting suspension was translucent. DLS measurements showed that the HPMCAS-126 nanoparticles remained at a constant size of around 150-160 nm for at least 6 hours (FIG. 2).

Figure 3:
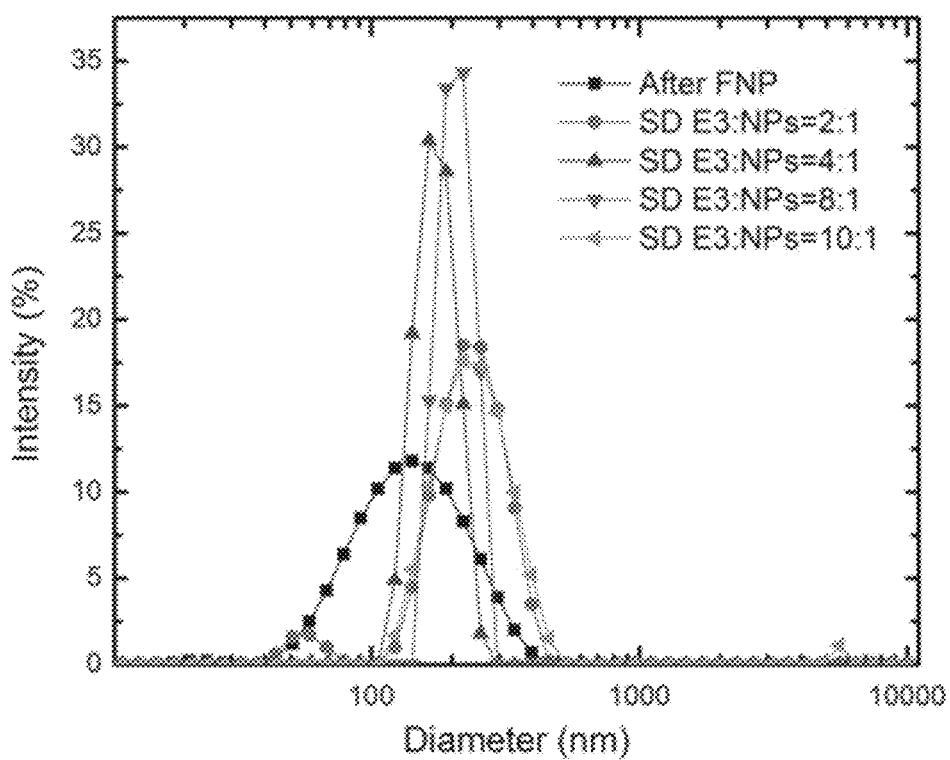
FIG. 3. Graph of DLS signal, indicating particle size distribution (PSD) of redispersed spray-dried samples.

The nanoparticle suspensions were spray-dried with HPMC E3 at the following excipient to nanoparticle weight ratios: 2:1, 4:1, 8:1, 10:1. For the spray-drying process, a Buchi Mini Spray Dryer B-290 was used with the following conditions: inlet temperature of 150° C., aspiration rate of 90%, spray gas flow rate at 355 L/hr (at standard temperature and pressure), and a sample feed rate of 6 mL/min. 3 mg of spray dried powders were then rehydrated with 1 mL MilliQ water and agitated by hand for 1 minute. DLS measurements were then made. The spray-dried powders were redispersed to nanoscale size (FIG. 3). The redispersed size went up by approximately 1.5 times compared with the original size in nanoparticle suspension right after FNP. By contrast, with lyophilization, the dried powders with the same weight ratio of excipient to nanoparticles could not be readily redispersed to nanoparticles, and formed large floating chunks instead.

Example 3: Lumefantrine-Loaded HPMCAS Nanoparticles

Lumefantrine (5 mg), as well as 5 mg of the stabilizers (HPMCAS 126, 716, 912) was added to 1 mL tetrahydrofuran (THF) to make the organic solution. (Lumefantrine has a molecular weight of 529 g/mol, solubility in water of about 0.031 mg/L, and a log P of about from 8.3 to 9.2.) This solution was Flash NanoPrecipitated against 1 mL MilliQ water into a 9 mL reservoir of stirring MilliQ water using a CIJ mixer. DLS measurements showed that three HPMCAS polymers were able to form lumefantrine loaded nanoparticles, with sizes ranging from 200 nm to 260 nm.

Figure 4:
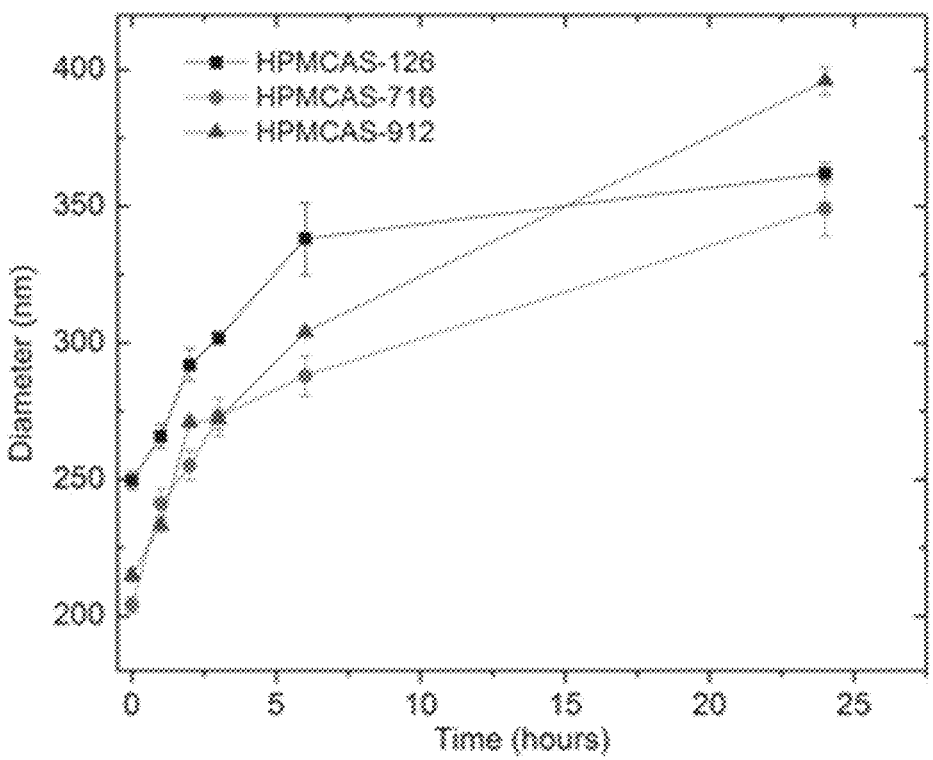
FIG. 4. Graph showing size stability of lumefantrine-loaded HPMCAS-126, HPMCAS-716, and HPMCAS-912 nanoparticles.

For HPMCAS-716/912 nanoparticles, the size swelled significantly after 6 hours compared with HPMCAS-126 nanoparticles (FIG. 4).

Example 4: Lyophilization and Redispersion of Lumefantrine-Loaded HPMCAS-126 Nanoparticles Lumefantrine (5 mg), as well as 5 mg of the stabilizer HPMCAS-126 was added to 1 mL tetrahydrofuran to make the organic solution. This solution was Flash NanoPrecipitated against 1 mL MilliQ water into a 9 mL reservoir of stirring MilliQ water using a CIJ mixer. DLS measurements gave the particle size as 249.7 nm.

Figure 5:
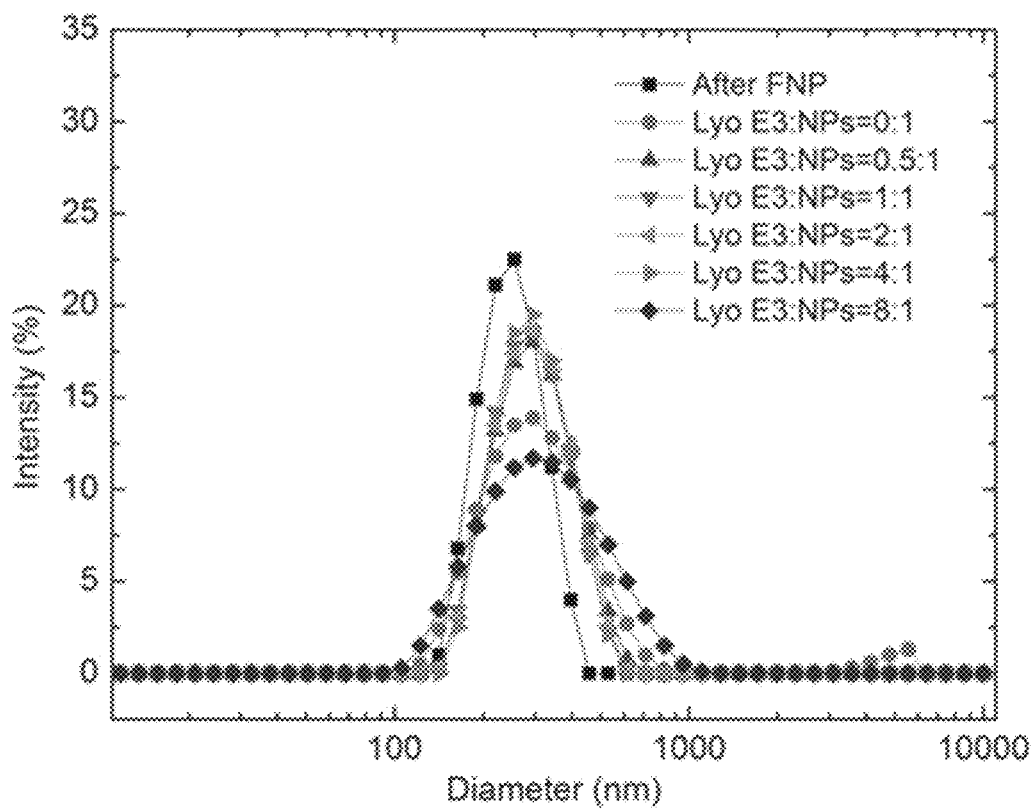
FIG. 5. Graph of DLS signal, indicating PSD of the redispersed lyophilized samples.

Aliquots of 1 mL of the nano-suspension were lyophilized with HPMC E3 at the following cryoprotectant to nanoparticle weight ratios: 0:1, 0.5:1, 1:1, 2:1, 4:1 and 8:1. Each sample was then rehydrated with 1 mL MilliQ water and agitated by hand for 1 minute. DLS measurements were then taken (FIG. 5).

All freeze-dried samples were redispersed to nanoparticles upon addition of MilliQ water, and the redispersed size went up to 1.2 times of the original batch.

Figure 6:
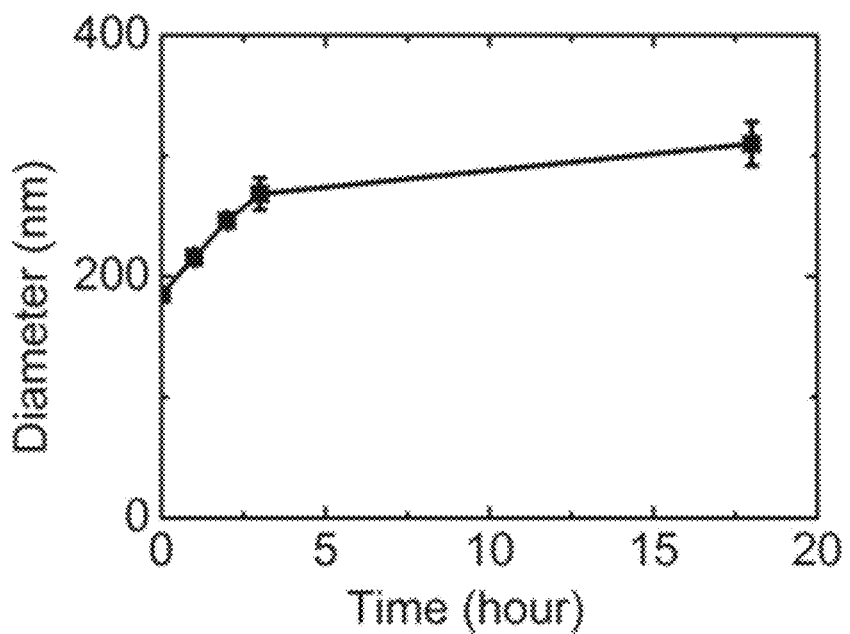
FIG. 6. Graph showing size stability of the HPMCAS-126 nanoparticles (NPs) loaded with lumefantrine.

Example 5: Spray-Drying and Redispersion of Lumefantrine-Loaded HPMCAS Nanoparticles Lumefantrine (75 mg) was added to 10 mL tetrahydrofuran (THF), as well as 37.5 mg of HPMCAS-126. This solution was flash nanoprecipitated using a MIVM, where the THF solution was pumped at 16 mL/min against three separate MilliQ water streams, each being pumped at 48 mL/min, for a 9:1 water:tetrahydrofuran ratio. The resulting suspension was translucent. DLS measurements showed that the HPMCAS-126 nanoparticles remained at a constant size of around 200-300 nm for at least 18 hours (FIG. 6).

Figure 7:
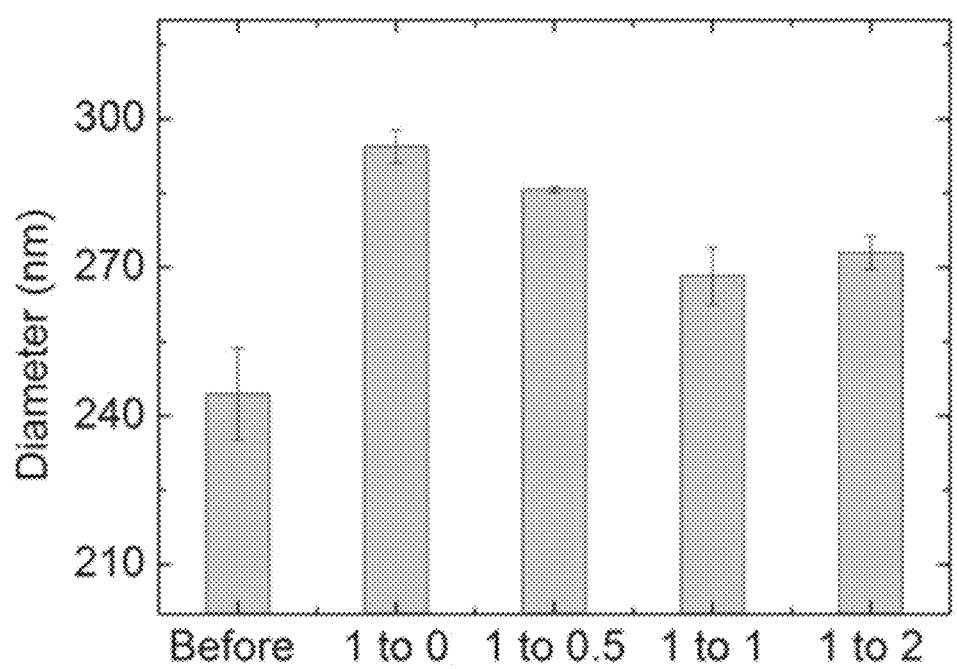
FIG. 7. Graph showing size of the redispersed spray-dried samples for different excipient to nanoparticle weight ratios.

The nanoparticle suspensions were spray-dried with HPMC E3 at the following excipient to nanoparticle weight ratios: 0:1, 0.5:1, 1:1, 2:1. For the spray drying process, Buchi Mini Spray Dryer B-290 was used with the following conditions: inlet temperature of 100° C., aspiration rate of 90%, spray gas flow rate at 350 L/hr (at standard temperature and pressure), and a sample feed rate of 5 mL/min. 3 mg of spray dried powders was then rehydrated with 1 mL MilliQ water and agitated by hand for 1 minute. DLS measurements were then taken. The spray-dried powders were redispersed to nanoscale size (FIG. 7). The redispersed size went up by approximately 1.2 times compared with the original size in nanoparticle suspension right after FNP.

Example 6: OZ439 Loaded HPMCAS Nanoparticles 5 mg of OZ439 (artefenomel) mesylate salt and 5 mg of one of the three stabilizers (HPMCAS 126, 716, 912) were added to 1 mL of a mixture of 33% methanol and 67% tetrahydrofuran. (OZ439 mesylate has a molecular weight of 566 g/mol, solubility in water of about 0.47 mg/L, and a log P of about from 4.5 to 5.4.) Also added to this solution was an amount of sodium oleate in a molar ratio of 1:1, 1:2, or 1:4 with OZ439 mesylate. 0.5 mL of this organic solution underwent Flash NanoPrecipitation against a stream of 0.5 mL MilliQ water via a CIJ mixer. During Flash NanoPrecipitation, the water-soluble OZ439 mesylate formed a hydrophobic complex with the sodium oleate through a counterion exchange process termed "hydrophobic ion pairing".

Figure 8A:
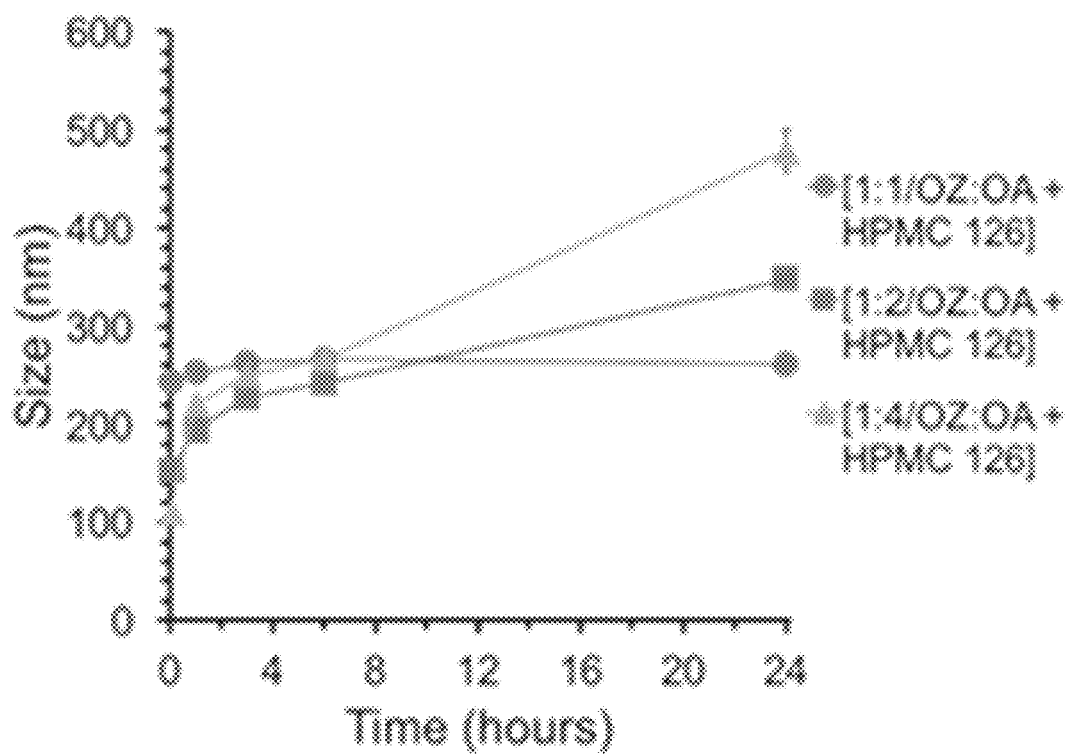
FIG. 8A. Graph showing size over time of the NPs containing ion-paired OZ439 stabilized by HPMCAS 126.
Figure 8B:
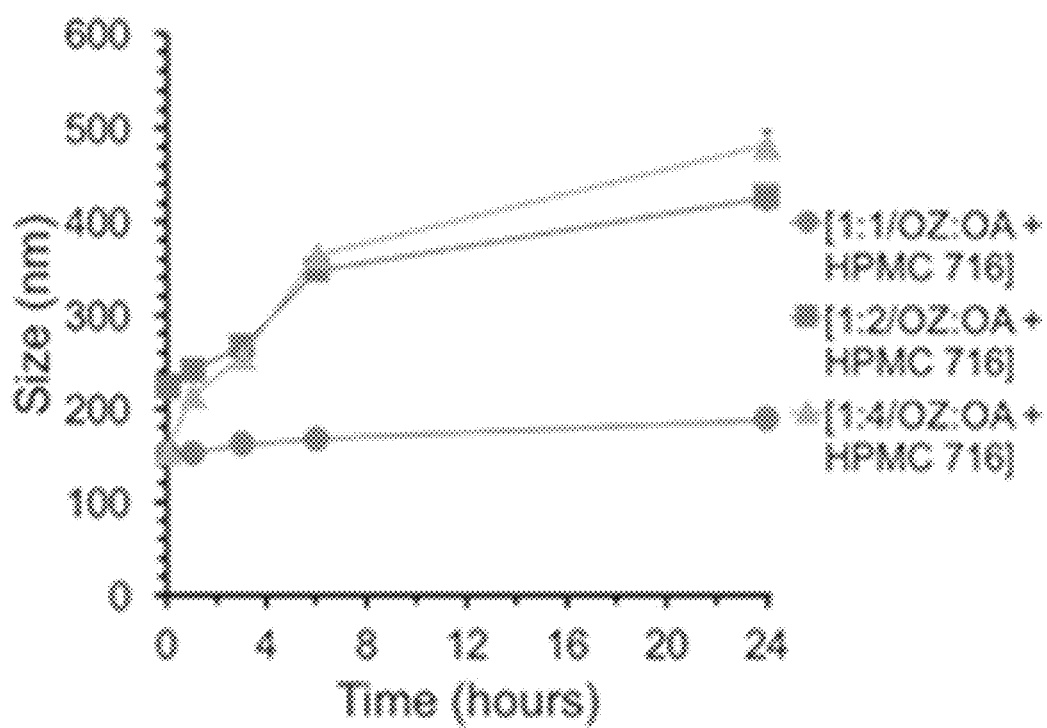
FIG. 8B. Graph showing size over time of the NPs containing ion-paired OZ439 stabilized by HPMCAS 716.
Figure 8C:
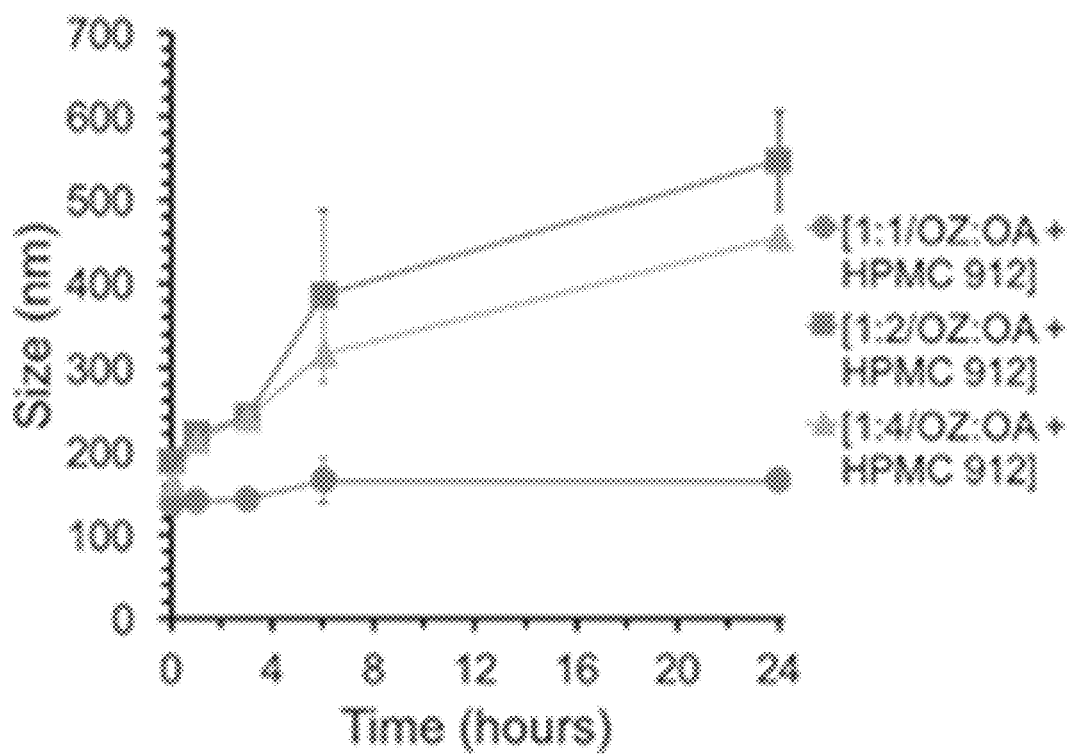
FIG. 8C. Graph showing size over time of the NPs containing ion-paired OZ439 stabilized by HPMCAS 912.
Figure 9A:
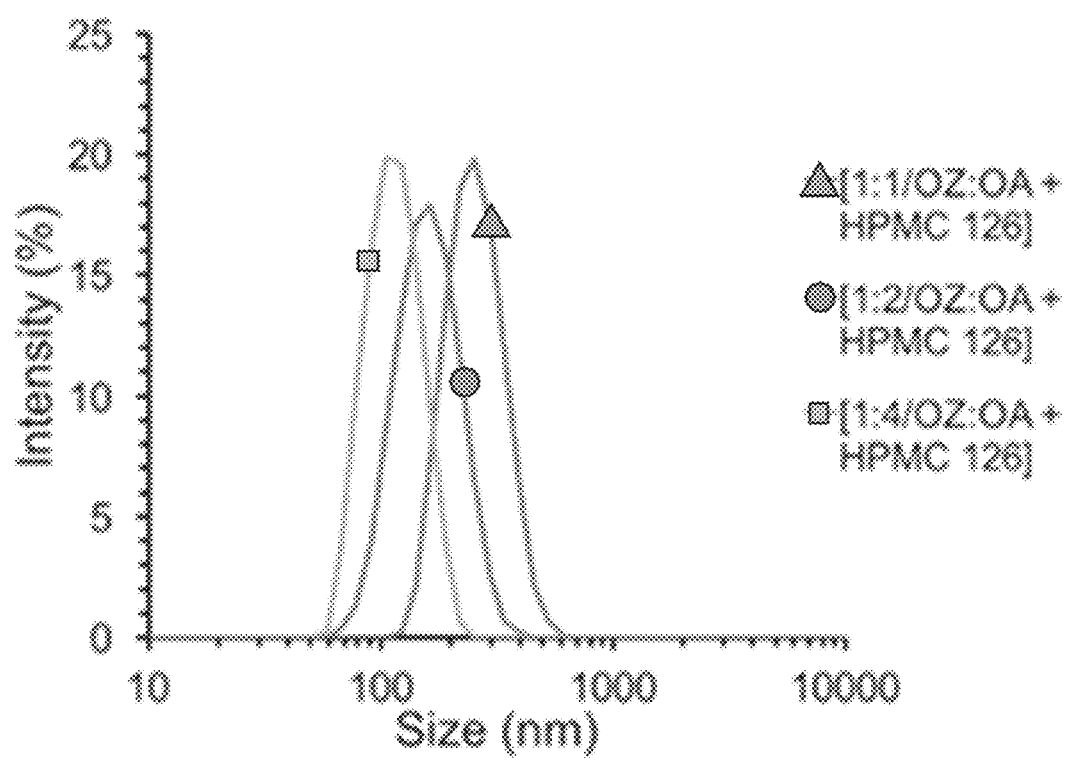
FIG. 9A. Graph of DLS signal, indicating particle size distribution (PSD) of HPMCAS 126-stabilized NPs made with varying ratios of OZ439 mesylate (OZ) to sodium oleate (OA). The mean size of the particles as determined by DLS was as follows: [1:1 OZ:OA+HPMC126]=120 nm; [1:2 OZ:OA+HPMC126]=175 nm; and [1:4 OZ:OA+HPMC126]=250 nm].
Figure 9B:
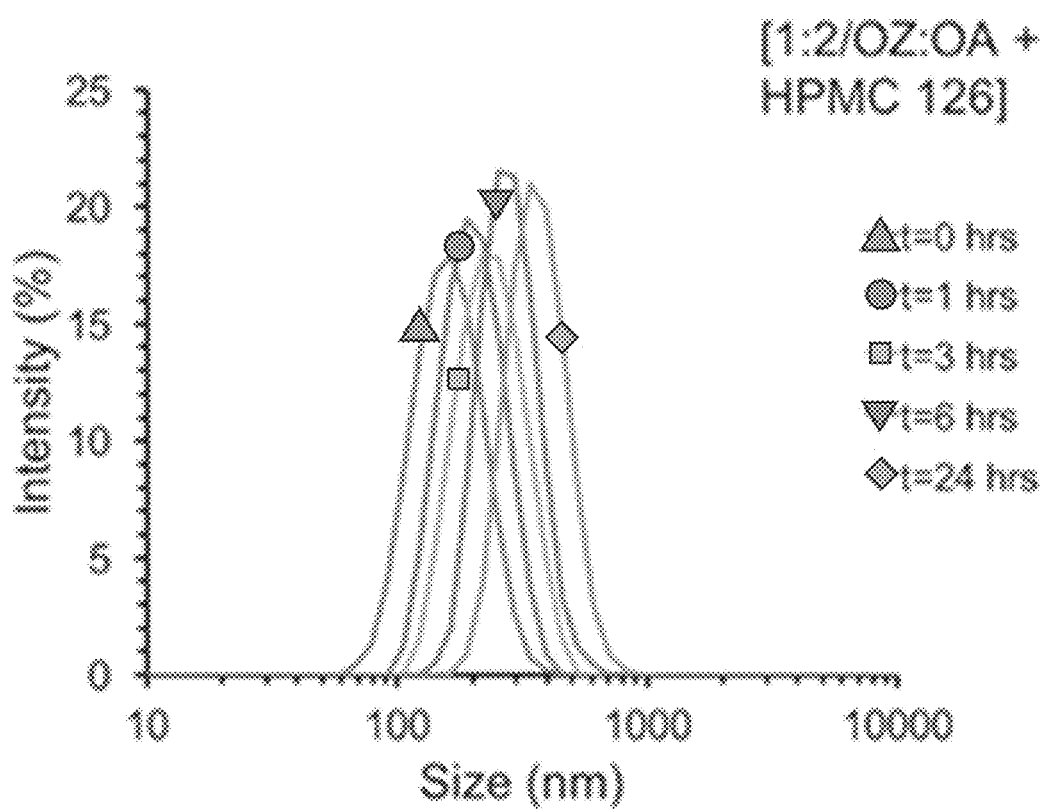
FIG. 9B. Graph of DLS signal, indicating PSD over time of HPMCAS 126-stabilized NPs made with a constant 1:2 ratio of OZ439 mesylate (OZ) to sodium oleate (OA) [1:2 OZ:OA+HPMC126]. The mean size of the particles as determined by DLS at several times was as follows: 175 nm at 0 hours; 200 nm at 1 hour; 240 nm at 3 hours; 280 nm at 6 hours; and 350 nm at 24 hours.

DLS measurements showed that three HPMCAS polymers were able to form OZ439 loaded nanoparticles, with sizes ranging from 100 nm to 250 nm. For HPMCAS-716/912 nanoparticles, the size swelled significantly after 6 hours compared with HPMCAS-126 nanoparticles (FIG. 8). FIG. 9A is a graph of DLS signal, indicating particle size distribution (PSD) of HPMCAS126-stabilized NPs made with varying ratios of OZ439 mesylate (OZ) to sodium oleate (OA). FIG. 9B shows how the PSD changes over time for the HPMCAS126-stabilized NPs made with a constant 1:2 ratio of OZ439 mesylate to sodium oleate.

Figure 10:
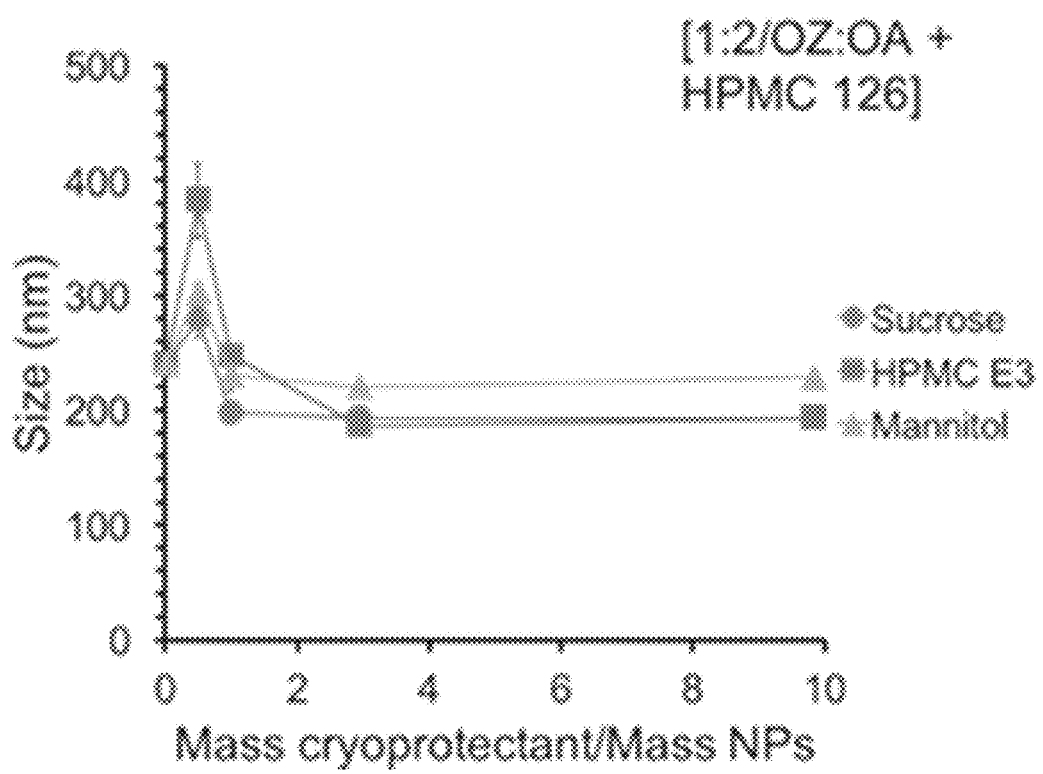
FIG. 10. Graph showing size of the redispersed lyophilized samples of NPs made with OZ439 and sodium oleate and stabilized by HPMCAS 126.

Aliquots of 1 mL of the nano-suspension were lyophilized with HPMC E3, sucrose, or mannitol at the following ratios of NPs (nanoparticles) to cryoprotectant: 1:0, 1:0.5, 1:1, 1:3 and 1:10. Each sample was then rehydrated with 1 mL MilliQ water and agitated by hand for 1 minute. DLS measurements were then taken (FIG. 10).

To investigate the effects of freezing on the nanoparticles' properties, each sample tested for lyophilization was also frozen and then thawed, and the nanoparticle characteristics were analyzed using DLS measurements. All samples tested, including those without any cryoprotectant, re-dispersed readily upon thawing.

Example 7: Cyclosporine a Loaded HPMCAS Nanoparticles 10 mg of Cyclosporine A (CSA) and 10 mg, 5 mg, 2.5 mg, or 1.25 mg of one of the three stabilizers (HPMCAS 126, 716, 912) were added to 1 mL of tetrahydrofuran. (Cyclosporine A has a molecular weight of 1203 g/mol, solubility in water of about from 6 to 12 mg/L, and a log P of about 3.6) 0.5 mL of this organic solution underwent Flash NanoPrecipitation against a stream of 0.5 mL MilliQ water via a CIJ mixer.

Figure 11A:
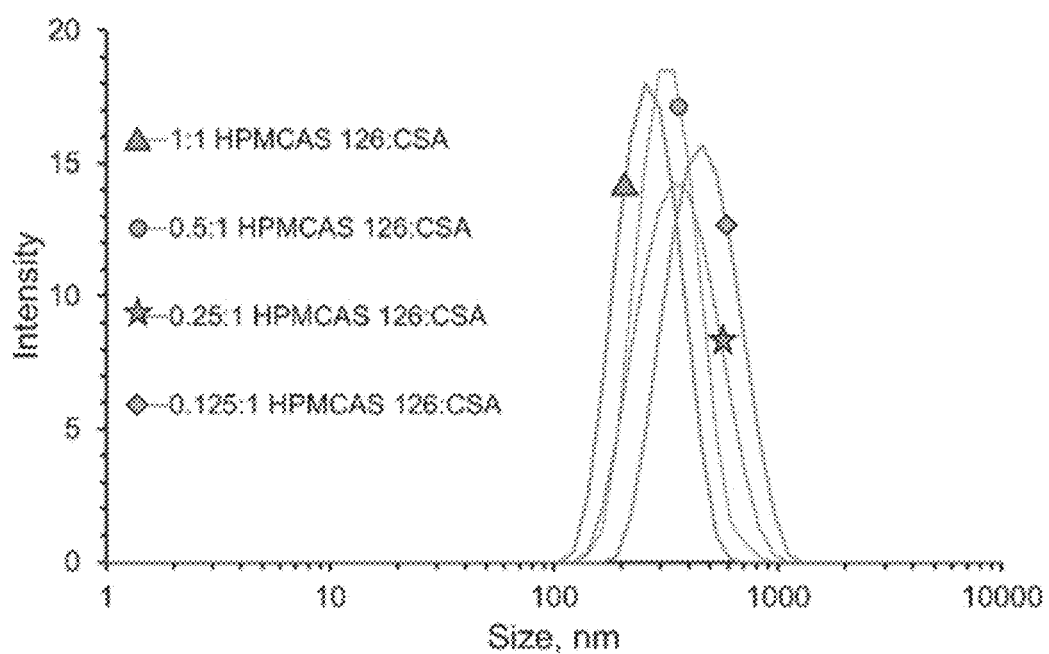
FIG. 11A. Graph of DLS signal, indicating PSD of HPMCAS 126-stabilized NPs made with CSA and varying ratios of HPMCAS stabilizer. The mean size of the particles as determined by DLS was as follows: [1:1 HPMCAS 126:CSA]=255 nm; [0.5:1 HPMCAS 126:CSA]=320 nm; [0.25:1 HPMCAS 126:CSA]=350 nm; and [0.125:1 HPMCAS 126:CSA]=460 nm.
Figure 11B:
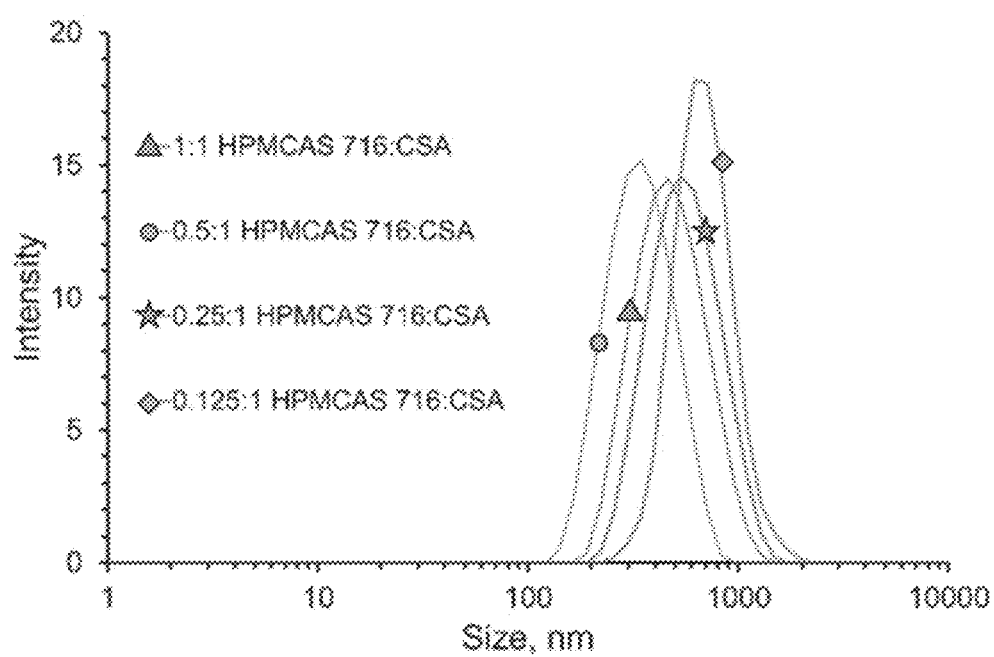
FIG. 11B. Graph of DLS signal, indicating PSD of HPMCAS 716-stabilized NPs made with CSA and varying ratios of HPMCAS stabilizer. The mean size of the particles as determined by DLS was as follows: [1:1 HPMCAS 716:CSA]=430 nm; [0.5:1 HPMCAS 716:CSA]=320 nm; [0.25:1 HPMCAS 716:CSA]=515 nm; and [0.125:1 HPMCAS 716:CSA]=670 nm.
Figure 11C:
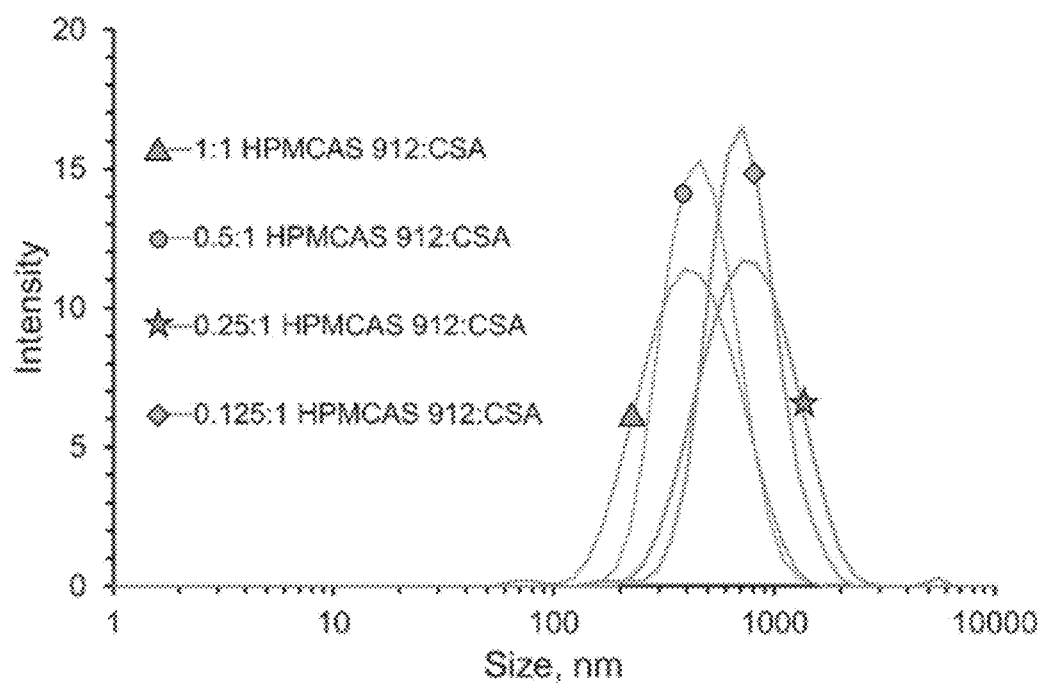
FIG. 11C. Graph of DLS signal, indicating PSD of HPMCAS 912-stabilized NPs made with CSA and varying ratios of HPMCAS stabilizer. The mean size of the particles as determined by DLS was as follows: [1:1 HPMCAS 912:CSA]=400 nm; [0.5:1 HPMCAS 912:CSA]=470 nm; [0.25:1 HPMCAS 912:CSA]=750 nm; and [0.125:1 HPMCAS 912:CSA]=700 nm.

DLS measurements showed that three HPMCAS polymers formed CSA loaded nanoparticles, with sizes ranging from 255 nm to 700 nm (FIG. 11). For example, nanoparticle sizes can range from 100 nm to 400 nm.

Example 8: Itraconazole Loaded HPMCAS Nanoparticles 5 mg of Itraconazole (ITZ) and 5 mg of one of the three stabilizers (HPMCAS 126, HPMCAS 716, and HPMCAS 912) were added to 1 mL of tetrahydrofuran. (Itraconazole has a molecular weight of 706 g/mol, solubility in water of about from 9.6 mg/L, and a log P of about from 5.5 to 7.3) 0.5 mL of this organic solution underwent Flash NanoPrecipitation (FNP) against a stream of 0.5 mL MilliQ water via a CIJ mixer.

Figure 12A:
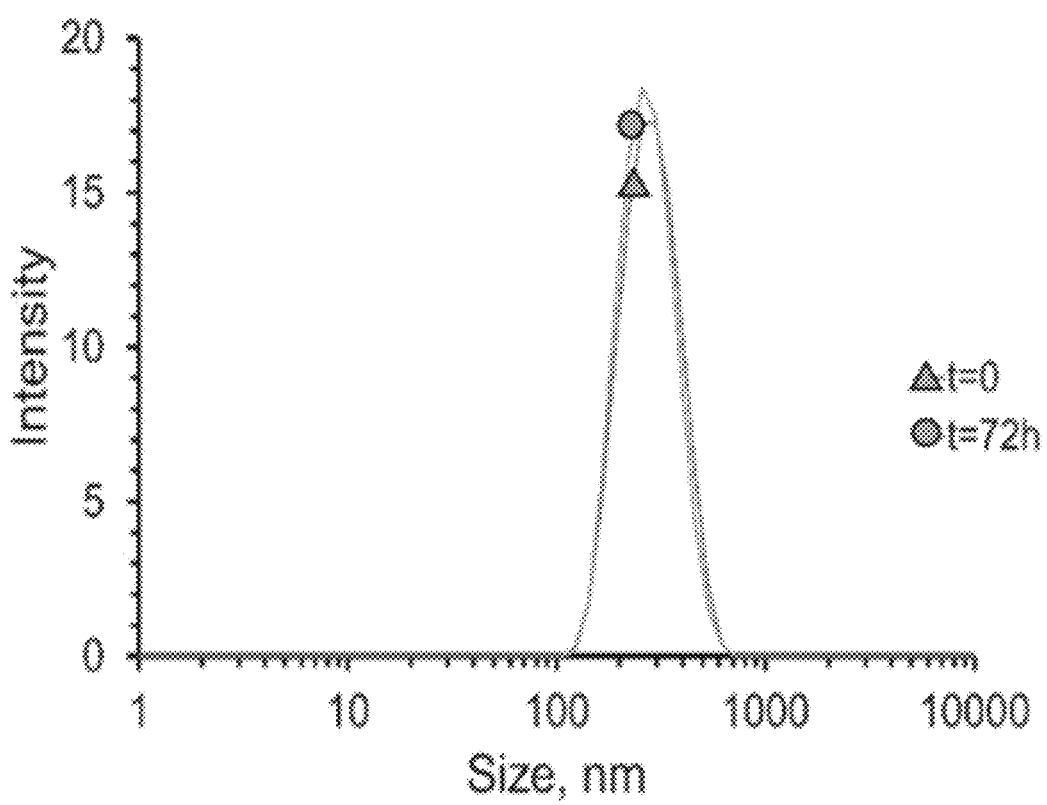
FIG. 12A. Graph of DLS signal, indicating PSD initially and after 72 h of HPMCAS126-stabilized NPs made with Itraconazole. The mean size of the particles as determined by DLS was as follows: 250 nm at 0 hours; and 250 nm at 72 hours.
Figure 12B:
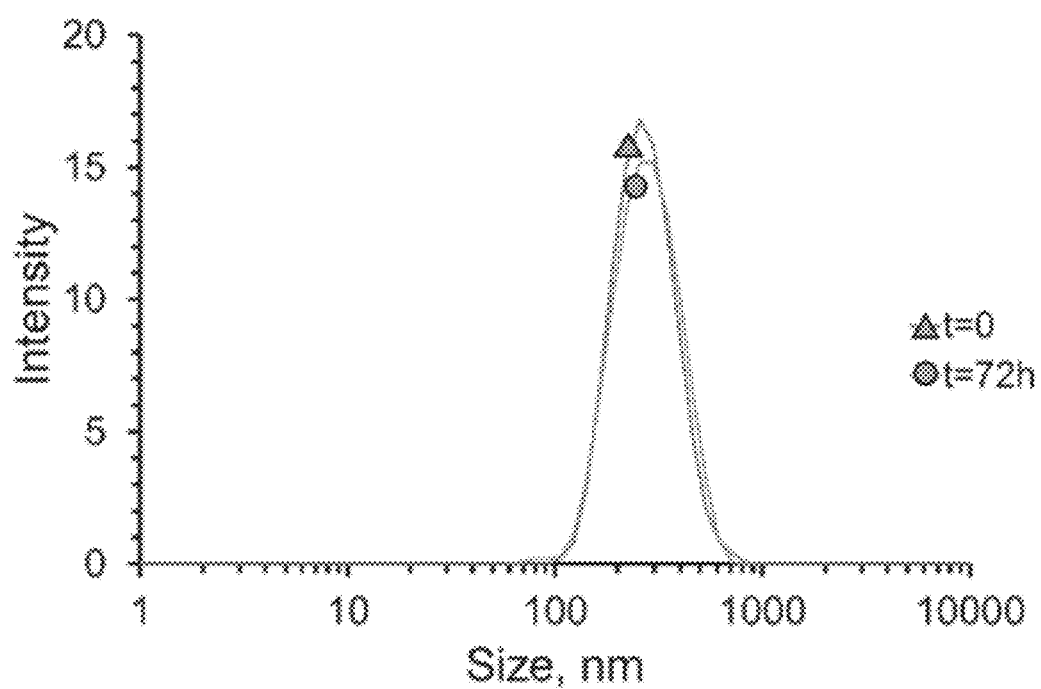
FIG. 12B. Graph of DLS signal, indicating PSD initially and after 72 h of HPMCAS716-stabilized NPs made with Itraconazole. The mean size of the particles as determined by DLS was as follows: 250 nm at 0 hours; and 300 nm at 72 hours.
Figure 12C:
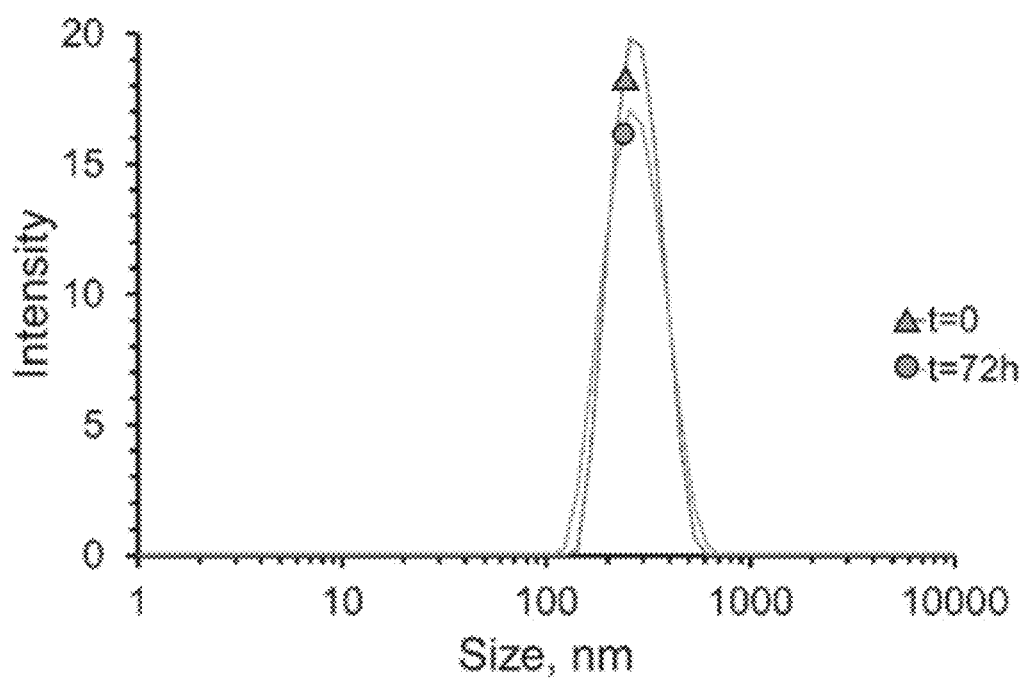
FIG. 12C. Graph of DLS signal, indicating PSD initially and after 72 h of HPMCAS912-stabilized NPs made with Itraconazole. The mean size of the particles as determined by DLS was as follows: 280 nm at 0 hours; and 280 nm at 72 hours.

DLS measurements showed that the three HPMCAS polymers were able to form ITZ loaded nanoparticles approximately 250 nm in size. For particles stabilized by all three HPMCAS, particles diluted 10× in water remained of the same size for 72 hours (h or hrs) (FIG. 12).

Figure 13:
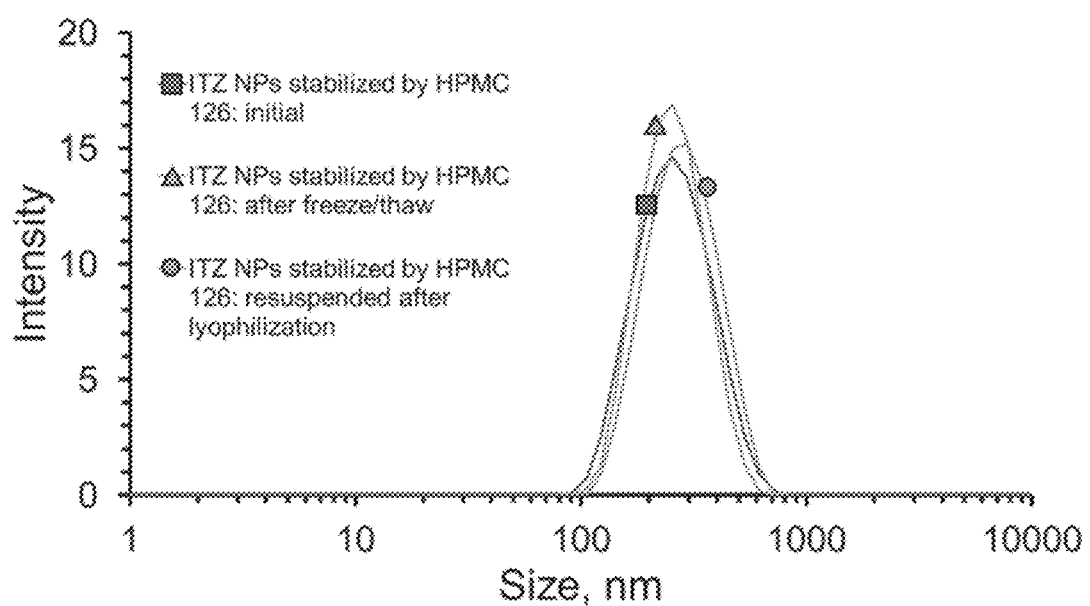
FIG. 13. Graph of DLS signal, indicating PSD initially and after freeze/thaw or lyophilization/resuspension of Itraconazole particles stabilized by HPMCAS 126. The mean size of the particles as determined by DLS was as follows: initial 250 nm; after freeze/thaw 250 nm; and after lyophilization/resuspension 300 nm.

The stability of Itraconazole particles stabilized by HPMCAS 126 through the freezing and lyophilization processes was measured. HPMCAS-126 ITZ particles retained their size after freeze/thaw with no cryoprotectant, and redispersed into nanoparticle form following lyophilization with no cryoprotectant (FIG. 13).

Example 9: ETTP5 Loaded HPMCAS Nanoparticles

HPMCAS has also been used to encapsulate a dye, ETTP5. 5 mg of HPMCAS 912, 10 mg of Vitamin E acetate, and 0.26 mg of ETTP5 were dissolved in Tetrahydrofuran. 0.5 mL of this organic solution underwent Flash NanoPrecipitation against a stream of 0.5 mL MilliQ water via a CIJ mixer.

Figure 14:
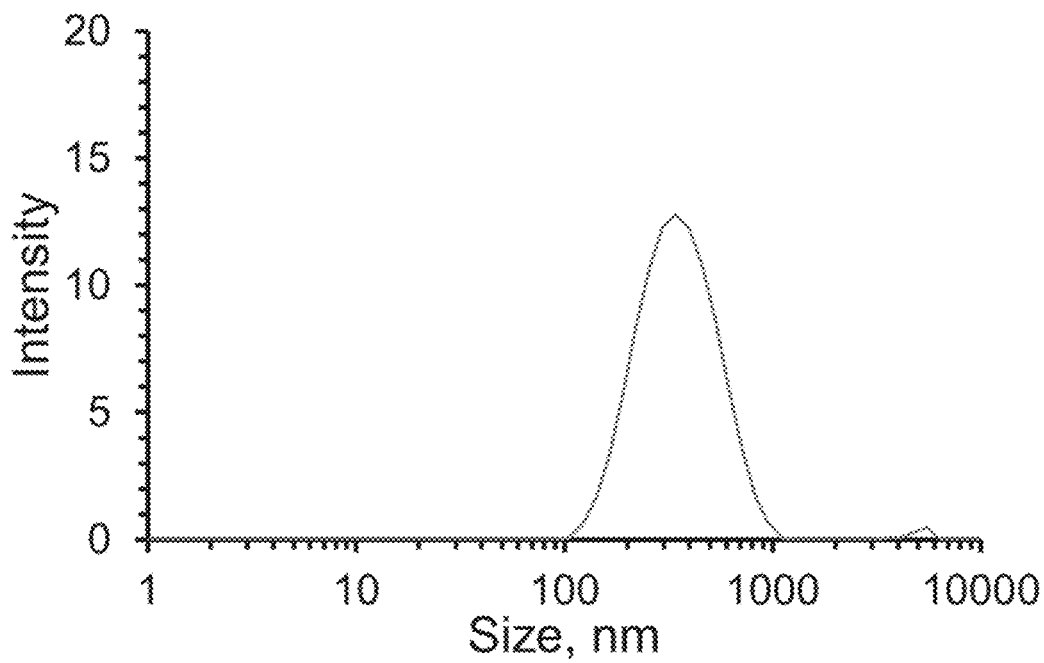
FIG. 14. Graph of DLS signal, indicating PSD of nanoparticles containing Vitamin E acetate and ETTP5 and stabilized by HPMCAS 912.

DLS measurements showed that ETTP5 loaded nanoparticles approximately 311 nm in size were formed (FIG. 14).

Example 10: HPMCAS Coating of Hydrophobic Nanoparticles Containing Lysozyme

In another embodiment of this invention, the hydrophobic material (hydrophobic active) may be a complex assembly of associated molecules. For example, the hydrophobic active may be a nanoparticle with a hydrophobic surface and be termed a hydrophobic-surface nanoparticle or a hydrophobic nanoparticle. These hydrophobic nanoparticles may be assembled by inverse Flash NanoPrecipitation (iFNP), which is described in International Application PCT/US2016/068145, which was published as WO/2017/112828 on Jun. 29, 2017, and which are incorporated by reference herein in their entirety. For example, in iFNP, a block copolymer, e.g., a block copolymer having at least one hydrophilic block and at least one hydrophobic block, and a hydrophilic material, such as a hydrophilic protein, peptide, or other molecule, can be dissolved in a polar solvent, such as water, alcohols such as methanol, ethanol, n-propanol, and isopropanol, acetonitrile, dimethyl sulfoxide (DMSO), and dimethylformamide (DMF), or mixtures of such polar solvents to form a polar solution. The polar solution can then be continuously mixed against a less polar solvent, i.e., a solvent that is less polar than the polar solvent in which the block copolymer and hydrophilic material were dissolved, such as dichloromethane (DCM), chloroform, tetrahydrofuran (THF), acetone, or mixtures of these, for example, in a Confined Impinging Jet (CIJ) device or a Multi-Inlet Vortex Mixer (MIVM). This can result in formation or precipitation of a nanoparticle that has a hydrophilic core, e.g., including a hydrophilic block of the copolymer and the hydrophilic molecule, and a hydrophobic exterior, e.g., a (hydrophobic) shell including the hydrophobic block of the copolymer, presented to the environment. These hydrophobic nanoparticles can then be used as the hydrophobic active (hydrophobic material) in the HPMCAS coating process.

A given solvent may be both in a list of solvents for use as a polar solvent and a list of solvents for use as a less polar solvent; the selection of a polar solvent for use and a less polar solvent for use can be made based on their relative polarity. For example, in some circumstances, acetone or an acetone-water mixture can be used as a polar solvent, if a less polar solvent is smaller as the less polar solvent. For example, a solvent that has a smaller dielectric constant, a smaller dipole moment, some smaller combination of dielectric constant and dipole moment, a smaller $\delta P$ (polar) Hansen solubility parameter, a smaller $\delta H$ (hydrogen bonding) Hansen solubility parameter, or a smaller combination of $\delta P$ and $\delta H$ than another solvent can be considered to be a "less polar solvent" relative to that other solvent.

For example, hydrophobic nanoparticles loaded with lysozyme can be prepared by iFNP.

Figure 15:
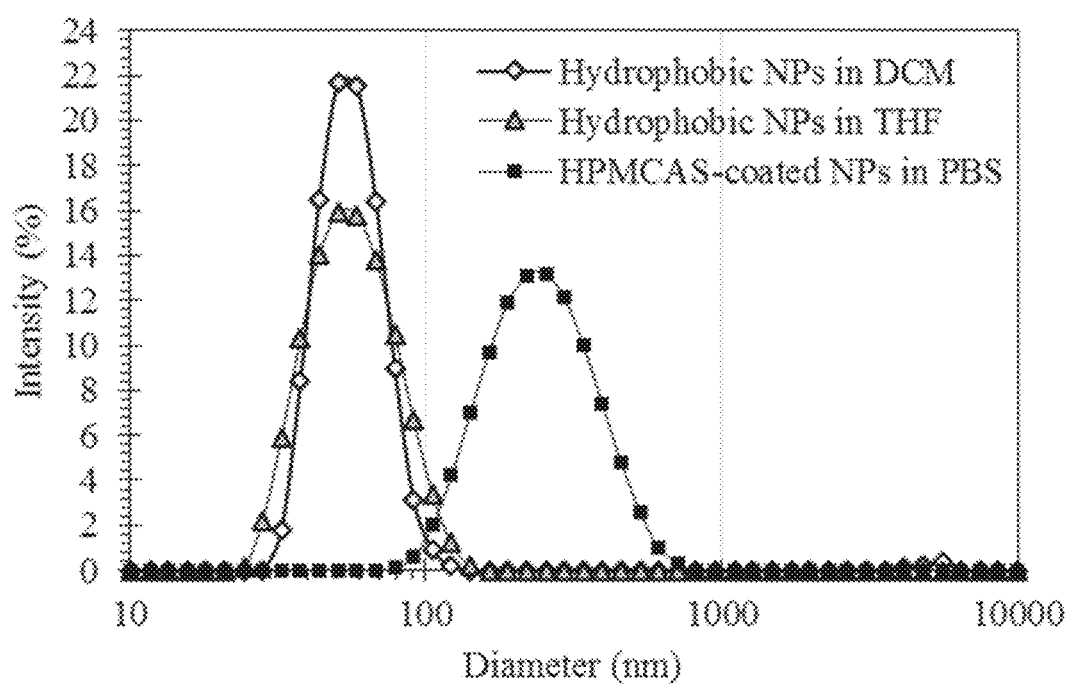
FIG. 15. Graph of DLS, indicating nanoparticle size distributions for the lysozyme-loaded hydrophobic nanoparticles in DCM and THF, and after coating with HPMCAS in PBS.

Lysozyme (2.5 mg) and poly(aspartic acid)-b-poly(lactic acid)-b-poly(aspartic acid) [PAsp(5 kDA)-b-PLA(20 kDa)-b-PAsp(5 kDa), 3.75 mg] were dissolved in 500 µL of dimethyl sulfoxide (DMSO) with 5 v % MilliQ water. In an iFNP process, this stream was rapidly mixed with 500 µL of dichloromethane (DCM) in a CIJ mixer and collected in a 4 mL stirring bath of DCM. This resulted in nanoparticles with a hydrophobic PLA surface and a core composed of PAsp and lysozyme. To the stirring suspension of nanoparticles, 58 µL of a 26.1 mM solution of tetraethylenepentamine (TEPA) in DCM was added dropwise. This corresponds to 0.7 equivalents of amine groups in the TEPA to acid groups in the PAsp. The TEPA ionically interacts with the PAsp, ionically crosslinking the core and stabilizing the particles during subsequent processing steps. The particles were mixed for 30 minutes to ensure full crosslinking. DLS measurements in DCM indicated that the hydrophobic nanoparticles were ~60 nm in diameter (FIG. 15).

In order to coat the particles with HPMCAS, a solvent-swap (solvent exchange) from DCM to a water-miscible solvent (tetrahydrofuran, THF) was first done. Three (3)

milliliters of a 150 mM brine solution was added on top of the nanoparticle dispersion to extract the DMSO from the DCM phase. The nanoparticles remained in the DCM phase, indicating their hydrophobic character. THF (5 mL) was added to the nanoparticle dispersion, and the particles were then concentrated to ~1 mL by rotary evaporation at 175 Torr and 40° C. DCM is more volatile than THF, therefore the nanoparticle solution is enriched with THF during evaporation. THF (9 mL) was again added to the nanoparticle dispersion and the particles were concentrated to ~1 mL by rotary evaporation at 150 Torr and 40° C. This THF addition and evaporation step was repeated twice more. The nanoparticle size did not change significantly through this solvent-swap process (FIG. 15).

Figure 16:
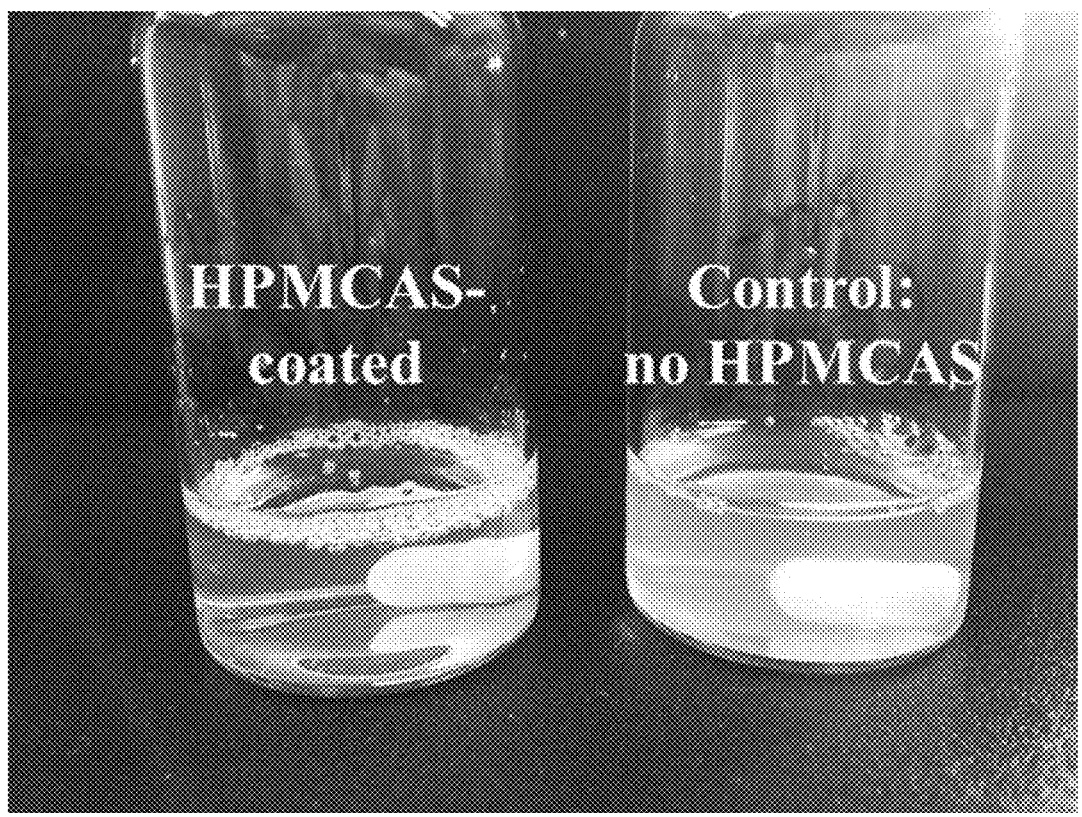
FIG. 16. Photograph of HPMCAS-coated hydrophobic nanoparticles with lysozyme in the core (left) and the control in which visible aggregates are present without HPMCAS (right).

The hydrophobic nanoparticles were then coated with HPMCAS-126. The THF stream (500 μL) contained 5 mg/mL of nanoparticles and 5 mg/mL of HPMCAS-126. This stream was rapidly mixed with 500 μL of phosphate-buffered saline (PBS) with a CIJ mixer and collected in a 4 mL stirring bath of PBS. The HPMCAS-coated nanoparticles were 260 nm in diameter (FIG. 15). This larger size suggests that there was some particle-particle aggregation and these nano-scale aggregates were coated with HPMCAS. The nanoparticle dispersion was opalescent and did not contain large visible aggregates (FIG. 16, left).

As a control, the hydrophobic nanoparticles (5 mg/mL in 500 μL of THF) without any HPMCAS-126 were rapidly mixed with 500 μL of PBS in a CIJ mixer and collected in a 4 mL stirring bath of PBS. Without HPMCAS, the hydrophobic particles aggregated, and large visible precipitates were present (FIG. 16, right).

Example 11: HPMCAS Coating of Hydrophobic Nanoparticles Containing Vancomycin

Figure 17:
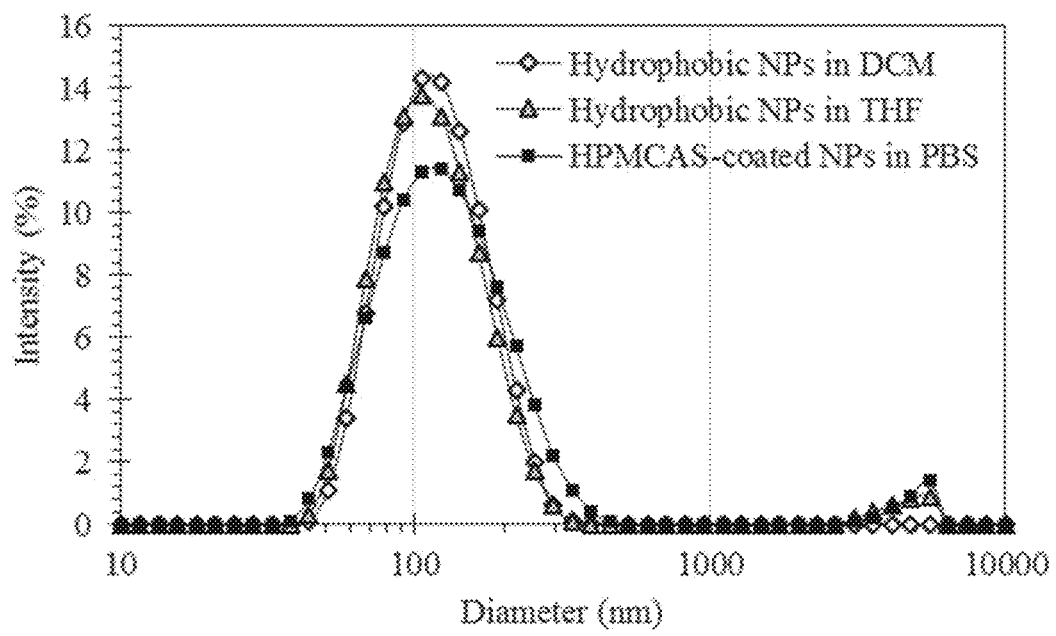
FIG. 17. Graph of DLS, indicating nanoparticle size distributions for the vancomycin-loaded hydrophobic nanoparticles in DCM and THF, and after coating with HPMCAS in PBS.

Hydrophobic nanoparticles loaded with vancomycin were produced by iFNP. Vancomycin (HCl salt) (2.5 mg) and PAsp(5 kDa)-b-PLA(20 kDa)-b-PAsp(5 kDa) (3.75 mg) were dissolved in 500 μL of DMSO with 5 v % MilliQ water. In an iFNP process, this stream was rapidly mixed with 500 μL of DCM in a CIJ mixer and collected in a 4 mL stirring bath of DCM. This resulted in nanoparticles with a hydrophobic PLA surface and a core composed of PAsp and vancomycin. To the stirring suspension of nanoparticles, 58 μL of a 26.1 mM solution of TEPA in DCM was added dropwise. This corresponds to 0.7 equivalents of amine groups in the TEPA to acid groups in the PAsp. The particles were mixed for 30 minutes to ensure full crosslinking. DLS measurements in DCM indicated that the hydrophobic nanoparticles were ~125 nm in size (FIG. 17).

A solvent-swap was conducted to take the nanoparticles from a DCM/DMSO mixture to THF. Three (3) milliliters of a 150 mM brine solution was added on top of the nanoparticle dispersion to extract the DMSO from the DCM phase. The nanoparticles remained in the DCM phase, indicating their hydrophobic character. THF (5 mL) was added to the nanoparticle dispersion, and the particles were then concentrated to ~1 mL by rotary evaporation at 175 Torr and 40° C. DCM is more volatile than THF, therefore the nanoparticle solution is enriched with THF during evaporation. THF (9 mL) was again added to the nanoparticle dispersion and the particles were concentrated to ~1 mL by rotary evaporation at 150 Torr and 40° C. This THF addition and evaporation step was repeated twice more. The nanoparticle size did not change significantly through this solvent-swap process (FIG. 17).

Figure 18:
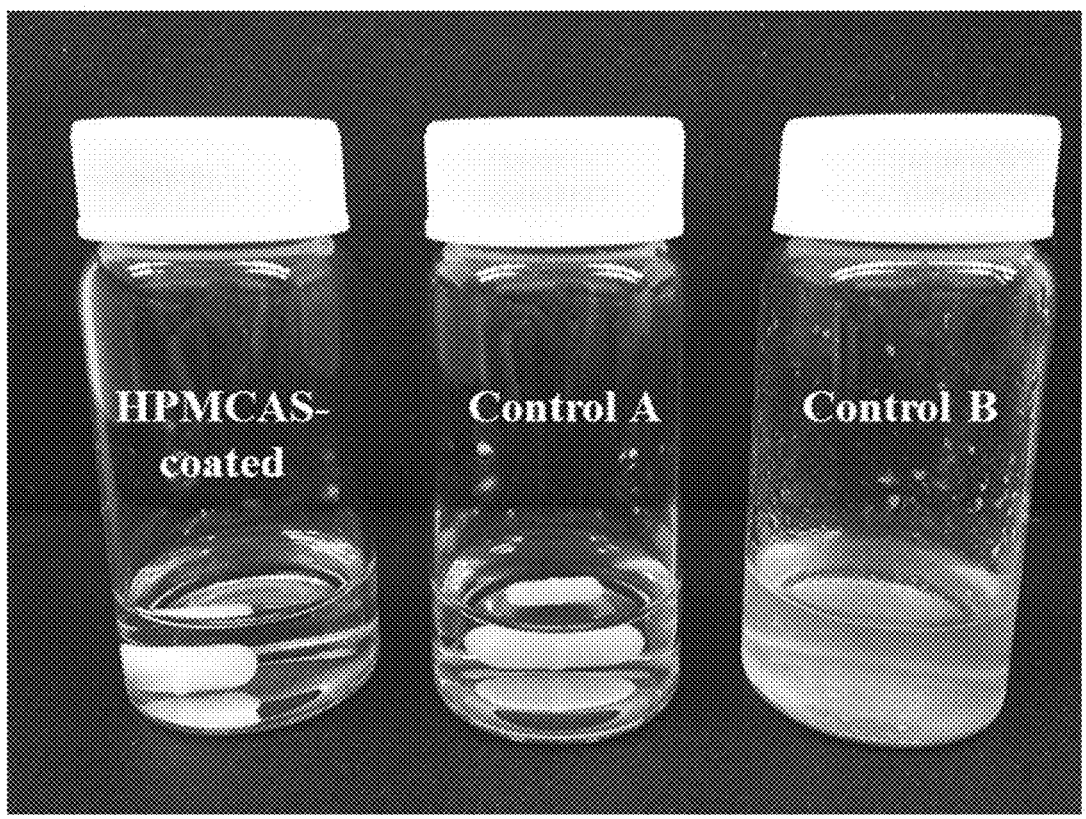
FIG. 18. Photograph of HPMCAS-coated hydrophobic nanoparticles with vancomycin in the core (left), Control A in which the particles did not aggregate but were smaller due to the lack of a HPMCAS coating (center), and Control B in which visible aggregates are present without HPMCAS (right).

The hydrophobic nanoparticles were then coated with HPMCAS-126. The THF stream (500 μL) contained 5 mg/mL of nanoparticles and 5 mg/mL of HPMCAS-126. This stream was rapidly mixed with 500 μL of phosphate-buffered saline (PBS) with a CIJ mixer and collected in a 4 mL stirring bath of PBS. The HPMCAS-coated nanoparticles were ~135 nm in diameter (10 nm larger than the original hydrophobic nanoparticles, FIG. 17). The nanoparticle was visibly transparent and did not contain large visible aggregates (FIG. 18, left).

As a control (Control A), the hydrophobic nanoparticles (5 mg/mL in 500 μL of THF) without any HPMCAS-126 were rapidly mixed with 500 μL of PBS in a CIJ mixer and collected in a 4 mL stirring bath of PBS. The particles did not visibly aggregate (FIG. 18, center) and were 10 nm smaller than the HPMCAS-coated particles due to the lack of coating (the same size as the hydrophobic nanoparticles in DCM). In a second control (Control B), the hydrophobic nanoparticles (10 mg/mL in 500 μL of THF) without any HPMCAS-126 were rapidly mixed with 500 μL of MilliQ water in a CIJ mixer and collected in a 4 mL stirring bath of MilliQ water. In this more concentrated control, without the HPMCAS the hydrophobic particles aggregated and large visible precipitates were present (FIG. 18, right).

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A nanoparticle comprising
   a cellulosic polymer substituted with hydrophilic groups; and
   a hydrophobic material,
   wherein the cellulosic polymer has a molecular weight from 10,000 to 2,000,000 g/mol and,
   wherein the nanoparticle has a size from 10 nm to 5000 nm,
   wherein the cellulosic polymer comprises a hydroxypropyl substitution level of from 5 to 10% wt, a methoxyl substitution level of from 20 to 26% wt, an acetyl substitution level of from 5 to 14% wt or from 10 to 14% wt, and a succinyl substitution level of from 4 to 18% wt or from 4 to 8% wt, and
   wherein the cellulosic polymer is a surface stabilizer around a core formed by the hydrophobic material.

2. The nanoparticle of claim 1, wherein the nanoparticle size does not change by more than 50% over 4 hours in aqueous solution.

3. The nanoparticle of claim 1, wherein the hydrophobic material has a molecular weight of from 800 to 5000 g/mol.

4. The nanoparticle of claim 1, wherein the hydrophobic material has a solubility in water of from 0.001 to 2 mg/L and a log P of from 7.5 to 12.

5. The nanoparticle of claim 1, wherein the hydrophobic material is selected from the group consisting of clofazimine, lumefantrine, cyclosporine A, artefenomel, artefenomel mesylate, and combinations.

6. A dispersion of nanoparticles of claim 1, wherein the dispersion is not an emulsion.

7. A process for forming a nanoparticle, comprising
dissolving a cellulosic polymer substituted with hydrophilic groups and a hydrophobic material in a less polar solvent to form a process solution, and
combining the process solution with a more polar solvent to rapidly precipitate the nanoparticle,
wherein the formed nanoparticle comprises the cellulosic polymer and the hydrophobic material,
wherein the cellulosic polymer is a surface stabilizer around a core formed by the hydrophobic material,
wherein the cellulosic polymer comprises a hydroxypropyl substitution level of from 5 to 10% wt, a methoxyl substitution level of from 20 to 26% wt, an acetyl substitution level of from 5 to 14% wt or from 10 to 14% wt, and a succinyl substitution level of from 4 to 18% wt or from 4 to 8% wt, and
wherein the cellulosic polymer has a molecular weight of from 10,000 to 2,000,000 g/mol.

8. The process of claim 7,
wherein the cellulosic polymer comprises a hydroxypropyl substitution level of from 5 to 10% wt, a methoxyl substitution level of from 20 to 26% wt, an acetyl substitution level of from 5 to 14% wt or from 10 to 14% wt, and a succinyl substitution level of from 4 to 18% wt or from 4 to 8% wt, and
wherein the cellulosic polymer has a molecular weight of from 20,000 to 2,000,000 g/mol.

9. The process of claim 8,
wherein the nanoparticle comprises an exterior hydrophilic shell,
wherein the exterior hydrophilic shell comprises the cellulosic polymer,
wherein the exterior hydrophilic shell surrounds the hydrophobic material.

10. The process of any one of claim 8,
wherein the process solution is in a process stream,
wherein the more polar solvent is in a more polar solvent stream,
wherein the process stream is continuously combined with the more polar solvent stream in a confined mixing volume, and
wherein the formed nanoparticle exits the confined mixing volume in an exit stream.

11. The process of claim 8,
wherein the less polar solvent is selected from the group consisting of acetone, an alcohol, methanol, ethanol, tetrahydrofuran, and combinations and
wherein the more polar solvent is water, an alcohol, or a water/alcohol combination.

12. The process of claim 8, further comprising
combining the formed nanoparticle with a water-soluble cellulosic polymer of hydroxypropyl and/or methyl substitution to form a further mixture, and
spray drying the further mixture to form a powder.

13. The process of claim 12, wherein the formed nanoparticle in the powder can be redispersed to within 20%, 30%, 50%, or 100% of its original size.

14. A process for forming a nanoparticle, comprising
dissolving a hydrophobic material in an organic solvent to form an organic solution,
dissolving a cellulosic polymer substituted with hydrophilic groups in an aqueous solvent to form an aqueous solution,
emulsifying the organic solution with the aqueous solution to form an emulsion, and
removing the organic solvent from the emulsion to form the nanoparticle by emulsion stripping,
wherein the formed nanoparticle comprises the cellulosic polymer as a surface stabilizer around a core formed by the hydrophobic material,
wherein the cellulosic polymer comprises a hydroxypropyl substitution level of from 5 to 10% wt, a methoxyl substitution level of from 20 to 26% wt, an acetyl substitution level of from 5 to 14% wt or from 10 to 14% wt, and a succinyl substitution level of from 4 to 18% wt or from 4 to 8% wt, and
wherein the cellulosic polymer has a molecular weight of from 10,000 to 2,000,000 g/mol.

15. The process of claim 14, further comprising
prior to dissolving the hydrophobic material in the organic solvent to form the organic solution, dissolving a block copolymer and a hydrophilic molecule in a preliminary polar solvent to form a preliminary polar solution, and
combining the preliminary polar solution with a preliminary less polar solvent to rapidly form a hydrophobic nanoparticle and a preliminary nanoparticle solvent,
wherein the hydrophobic nanoparticle is the hydrophobic material,
wherein the block copolymer comprises a hydrophobic block and a hydrophilic block,
wherein the hydrophobic nanoparticle comprises a surface that is hydrophobic,
wherein a hydrophilic core of the hydrophobic nanoparticle comprises the hydrophilic block,
wherein the hydrophilic core comprises the hydrophilic molecule,
wherein a preliminary nanoparticle solution comprises the hydrophobic nanoparticle and the preliminary nanoparticle solvent, and
wherein the preliminary less polar solvent is less polar than the preliminary polar solvent.

16. The process of claim 15, wherein the block copolymer comprises a triblock copolymer of a hydrophobic center block and two hydrophilic outer blocks.

17. The process of claim 15,
wherein the hydrophobic block is selected from the group consisting of poly(lactic acid), poly(lactic-co-glycolic acid), poly(caprolactone), and combinations and
wherein the hydrophilic block is selected from the group consisting of poly(aspartic acid), poly(glutamic acid), and combinations.

18. The process of claim 15, wherein the block copolymer comprises poly(aspartic acid)-b-poly(lactic acid)-b-poly(aspartic acid).

19. The process of claim 15,
wherein the preliminary polar solvent is selected from the group consisting of water, dimethyl sulfoxide (DMSO), and combinations and
wherein the preliminary less polar solvent is selected from the group consisting of dichloromethane, chloroform, and combinations.

20. The process of claim 15, further comprising adding a crosslinking agent to the preliminary nanoparticle solution to crosslink the hydrophilic block in the hydrophilic core.

21. The process of claim 15, further comprising exchanging the preliminary nanoparticle solvent with the less polar solvent.

22. The process of claim 15, wherein the hydrophilic molecule is of a molecular weight ranging from 100 g/mol to 40,000 g/mol, from 200 g/mol to 1500 g/mol, from 1000 g/mol to 40,000 g/mol, from 5000 g/mol to 40,000 g/mol, or from 5000 g/mol to 25,000 g/mol.

23. The process of claim 15, wherein the hydrophilic molecule comprises vancomycin or lysozyme.

24. The process of claim 15,
wherein the hydrophobic nanoparticle comprises a shell and
wherein the shell comprises the surface that is hydrophobic and the hydrophobic block.

25. The process of claim 15, wherein in the formed nanoparticle the cellulosic polymer encapsulates the hydrophobic nanoparticle.

26. The nanoparticle of claim 15,
wherein the hydrophobic block of the block copolymer is of a molecular weight of from 5 kDa to 40 kDa and
wherein the hydrophilic block of the block copolymer is of a molecular weight of from 2 kDa to 20 kDa.

* * * * *